United States Patent
Yu et al.

(10) Patent No.: US 11,549,129 B2
(45) Date of Patent: Jan. 10, 2023

(54) METHOD FOR PRODUCING POLYHYDROXYALKANOATES (PHA) FROM ORGANIC WASTE

(71) Applicant: GENECIS BIOINDUSTRIES INC., Toronto (CA)

(72) Inventors: Luna Yu, Scarborough (CA); Hasitha de Alwis Weerasekera, Toronto (CA); Marcos Forattini Lemos Igreja, Scarborough (CA); Vani Sankar, Scarborough (CA); Michael James Williamson, Toronto (CA); Sudhanshu Sanjay Soman, Toronto (CA); Kaitlyn Chow, Scarborough (CA)

(73) Assignee: Genecis Bioindustries Inc., Scarborough (CA)

( * ) Notice: Subject to any disclaimer, the term of this patent is extended or adjusted under 35 U.S.C. 154(b) by 0 days.

(21) Appl. No.: 16/230,660

(22) Filed: Dec. 21, 2018

(65) Prior Publication Data
US 2019/0203237 A1  Jul. 4, 2019

Related U.S. Application Data

(60) Provisional application No. 62/608,923, filed on Dec. 21, 2017.

(51) Int. Cl.
| | | |
|---|---|---|
| C12P 7/62 | (2022.01) | |
| C12M 1/00 | (2006.01) | |
| C12M 1/26 | (2006.01) | |
| C12P 7/625 | (2022.01) | |
| C12M 1/33 | (2006.01) | |

(52) U.S. Cl.
CPC ............ *C12P 7/62* (2013.01); *C12M 21/12* (2013.01); *C12M 29/00* (2013.01); *C12M 33/14* (2013.01); *C12M 45/02* (2013.01); *C12P 7/625* (2013.01)

(58) Field of Classification Search
CPC ................................ C12P 7/625; C08G 63/06
See application file for complete search history.

(56) References Cited

U.S. PATENT DOCUMENTS

| | | | | |
|---|---|---|---|---|
| 7,141,400 B2 | 11/2006 | Yu | | |
| 2008/0234210 A1* | 9/2008 | Rijn | .......... | A23B 7/155 514/28 |
| 2012/0305478 A1* | 12/2012 | Werker | .......... | C02F 3/34 210/608 |
| 2013/0005950 A1* | 1/2013 | Moya | .......... | C12M 23/28 530/387.3 |
| 2014/0224829 A1* | 8/2014 | Capone | .......... | B05B 11/3015 222/23 |
| 2015/0060356 A1* | 3/2015 | Barry | .......... | C05F 17/90 210/603 |
| 2015/0367285 A1* | 12/2015 | Chang | .......... | B01D 61/025 210/652 |
| 2016/0145659 A1* | 5/2016 | Anderson | .......... | C12P 7/625 435/3 |
| 2016/0251474 A1 | 9/2016 | Nouaille et al. | | |
| 2016/0355849 A1 | 12/2016 | Stephanopoulos et al. | | |
| 2017/0002385 A1 | 1/2017 | Yu | | |
| 2017/0198314 A1 | 7/2017 | Dijkman et al. | | |

FOREIGN PATENT DOCUMENTS

| | | | | |
|---|---|---|---|---|
| WO | WO-2012166822 A2 * | 12/2012 | .......... | C12P 7/625 |
| WO | WO-2015133887 A1 * | 9/2015 | .......... | C12P 7/625 |
| WO | 2016/081902 A1 | 5/2016 | | |

OTHER PUBLICATIONS

Millipore/sigma webpage for "pore size or nomainal moelcular weight" downloaded from https://www.emdmillipore.com/US/en/life-science-research/chromatography-sample-preparation/membrane-learning-center/Pore-Size-or-NMWL on May 10, 2020 (Year: 2020).*
Val del Rio et al. Water Research (2011) 45: 6011-6020 (Year: 2011).*
Fradinho et al. J. Biotechnol. (2014; 185: 19-27 (Year: 2014).*
Izumi et al. Int. Biodeterioration Beidegradation (2010) 64: 601-608 (Year: 2010).*
Kozuchowska et al. Environmental Technol. (1995) 16: 667-675 (Year: 1995).*
Oliveira, C.S.S., et al., "Strategies for efficiently selecting PHA producing mixed microbial cultures using complex feedstocks: feast and famine regime and uncoupled carbon and nitrogen availabilities", N. Biotechnol., Jul. 25, 2017 (Jul. 25, 2017), vol. 37, pp. 69-79, ISSN 1871-6784.
Reis, M.A.M., et al., "Production of polyhydroxyalkanoates by mixed microbial cultures". Bioprocess Biosyst. Eng., 2003, vol. 25, Issue 6, pp. 377-385, ISSN 1615-7591 *p. 383; Table 2*.
Valentino, F., et al., "Carbon recovery from wastewater through bioconversion into biodegradable polymers", N. Biotechnol., Jul. 25, 2017 (Jul. 25, 2017), vol. 37, pp. 9-23, ISSN 1871-6784 *abstract; p. 11; Fig. 1*.

(Continued)

*Primary Examiner* — Susan M Hanley
(74) *Attorney, Agent, or Firm* — Bereskin & Parr LLP/S.E.N.C.R.L., s.r.l.

(57) ABSTRACT

According to one broad aspect of this disclosure, a method is provided for producing polyhydroxyalkanoates (PHA) from organic waste. The method comprises homogenizing organic waste to obtain a feedstock that has 1:1 to 3:1 (w/w) water to organic waste ratio. The feedstock is inoculated with an inoculum of acidogenic fermentative bacteria in order to obtain an inoculated feedstock. The inoculated feedstock is incubated for 5 to 10 days, 3 to 10 days, optionally 7 days, optionally 3 days, to obtain a fermentation broth. The fermentation broth comprises volatile fatty acids (VFAs) and undigested organic waste. The fermentation broth is filtered with a filter with a pore size ranging from 0.2 μm to 500,000 NMWC to remove the acidogenic fermentative bacteria and undigested organic waste, to obtain a clarified broth comprising concentrated VFAs. The clarified broth and high-PHA producing bacteria are incubated to produce intracellular PHA granules in the high-PHA producing bacteria. PHA polymers are extracted from the intracellular PHA granules.

16 Claims, 23 Drawing Sheets

(56) References Cited

OTHER PUBLICATIONS

Hahn, S.K., et al., "The recovery of poly(3-hydroxybutrate) by using dispersions of sodium hypochlorite solution and chloroform", Biotechnol. Tech., Mar. 1993 (Mar. 1993), vol. 7, No. 3, pp. 209-212, ISSN 0951-208X.

Valentino, F., et al., "Polyhydroxyalkanoate (PHA) storage within a mixed-culture biomass with simultaneous growth as a function of accumulation substrate nitrogen and phosphorus levels", Water Res., 2015, vol. 77, pp. 49-63, ISSN 0043-1354.

Serafim, L.S., et al., "Strategies for PHA production by mixed cultures and renewable waste materials", Appl. Microbiol. Biotechnol., 2008, vol. 81, pp. 615-628, ISSN 0175-7598.

Colombo et al., "Enhanced polyhydroxyalkanoate (PHA) production from the organic fraction of municipal solid waste by using mixed microbial culture", Biotechnollogy for Biofuels, (2017) 10:201.

Du et al., "Green Technology for Conversion of Food Scraps to Biodegradable Thermoplastic Polyhydroxyalkanoates", Environmental Science & Technology, 2002, 36 (24), 5511-5516.

Platt, "iGEM team's poop-to-plastic concept wins international gold medal", (http://www.ucalgary.ca/utoday/issue/2017-12-07/igem-teams-poop-plastic-concept-wins-international-gold-medal), Dec. 7, 2017.

Igem HQ, "Team Calgary: Our Project", Online, (http://2017.igem.org/Team:Calgary/Description; http://2017.igem.org/wiki/index.php?title=Team:Calgary&offset=&limit=500&action=history), Apr. 4, 2017.

Ariunbaatar, J., et al., "Pretreatment methods to enhance anaerobic digestion of organic solid waste." Applied Energy, 2014, pp. 143-156, 123.

Lee, W.S., et al., "A review of the production and applications of waste-derived volatile fatty acids." (Accepted Manuscript) Chemical Engineering Journal, 2014, pp. 83-99, vol. 235.

Rhu, D.H., et al., "Polyhydroxyalkanoate (PHA) production from waste." Water Science and Technology, 2003, pp. 221-228, vol. 48, No. 8.

Zhang, M., et al., "Coupling of polyhydroxyalkanoate production with volatile fatty acid from food wastes and excess sludge." Process Safety and Environmental Protection, 2014, pp. 171-178, 92.

Villano, M., et al., "Effect of pH on the production of bacterial polyhydroxyalkanoates by mixed cultures enriched under periodic feeding." Process Biochemistry, 2010, pp. 714-723, 45.

Kasemsap, C., and Wantawin, C., "Batch production of polyhydroxyalkanoate by low-polyphosphate-content activated sludge at varying pH." Bioresource Technology, 2007, pp. 1020-1027, 98.

Serafim, L.S., et al., "Optimization of Polyhydroxybutyrate Production by Mixed Cultures Submitted to Aerobic Dynamic Feeding Conditions." Biotechnol Bioeng., Jul. 20, 2004;87(2):145-60. doi: 10.1002/bit.20085.

Albuquerque, M.G.E., et al., "Strategies for the development of a side stream process for polyhydroxyalkanoate (PHA) production from sugar cane molasses." Journal of Biotechnology, 2007, pp. 411-421, 130.

* cited by examiner

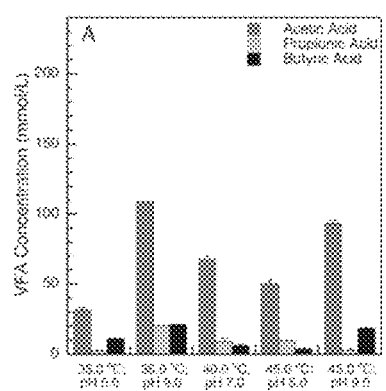 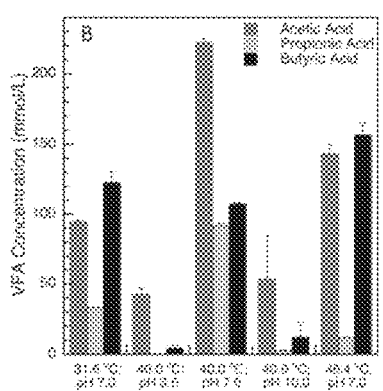 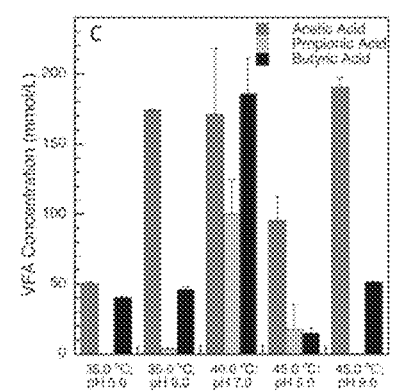
FIG. 14A  FIG. 14B  FIG. 14C

METHOD FOR PRODUCING POLYHYDROXYALKANOATES (PHA) FROM ORGANIC WASTE

CROSS-REFERENCE TO RELATED APPLICATION

This application claims the benefit of United States Provisional Patent Applications U.S. Ser. No. 62/608,923 filed Dec. 21, 2017 herein incorporated by reference.

FIELD

The described embodiments relate to methods and apparatus for producing polyhydroxyalkanoates (PHA) from organic waste.

BACKGROUND

The adverse environmental impacts of petroleum-based plastic waste have raised a critical worldwide concern. Thus, the worldwide demand for bioplastics has increased significantly and is estimated to be a 1-billion-dollar global industry in 2017. Polyhydroxyalkanoates (PHAs) are biopolyesters that include polyhydroxybutyrate (PHB), polyhydroxyvalerate (PHV), and polyhydroxyhexonate (PHH). These thermoplastic polymers are significantly versatile and have a wide spectrum of properties that can be achieved by manipulating the monomer composition, polymer molecular weight (MW) and crystallinity which can ultimately determine the polymer's mechanical and thermal properties, and hence the potential application. Many factors such as the types of microbes, carbon feedstock and growth parameters (i.e. carbon/nitrogen (C/N) ratio, dissolved oxygen content, and pH) can influence the polymer composition. PHAs are also biocompatible and biodegradable, and are a promising alternative for conventional petroleum-based plastics with their added environmental and biomedical benefits.

PHAs are synthesized as an intracellular energy storage mechanism in a wide range of bacterial species. Biosynthesis of PHA can be induced by subjecting PHA-producing microbes to carbon-rich and nitrogen- and phosphorous-limiting conditions. Current commercial PHA production relies on sugar- or plant oil-based feedstock. In addition to their high cost, the use of agricultural products for bioplastic production raises issues of land use and competition with food production. Organic waste is a potential alternate feedstock that avoids these issues and can be obtained at low or negative cost. The use of organic waste as a feedstock also results in diversion of these wastes from landfills, where they decompose and contribute significantly to global greenhouse gas emissions. Before use as a feedstock for PHA production, organic waste must undergo hydrolysis and acidogenesis. During this process, controlled mixed microbial cultures convert the organic waste into volatile fatty acids (VFAs), which can be utilized as a carbon source by PHA-producing bacteria.

SUMMARY OF THE DISCLOSURE

The following is intended to introduce the reader to the more detailed discussion to follow. The summary is not intended to limit or define the claims.

According to one broad aspect of this disclosure, a method is provided for producing polyhydroxyalkanoates (PHA) from organic waste. The method comprises homogenizing organic waste to obtain a feedstock that has 1:1 to 3:1 (w/w) water to organic waste ratio. The feedstock is inoculated with an inoculum of acidogenic fermentative bacteria in order to obtain an inoculated feedstock. These acidogenic bacteria may include genetically modified bacteria or wild-type bacteria that are naturally occurring with characteristics of moderately thermophilic, anaerobic, fermentative bacteria. These bacteria may consist of both facultative anaerobes and strict anaerobes. The inoculated feedstock is incubated for 5 to 10 days, optionally 3 to 10 days, optionally 7 days, optionally 3 days, or optionally 5 days to obtain a fermentation broth. The fermentation broth comprises volatile fatty acids (VFAs) and undigested organic waste. The fermentation broth is filtered with a filter with a pore size ranging from 0.2 µm to 500,000 NMWC, optionally 0.2 µm to 300,000 NMWC, to remove the acidogenic fermentative bacteria and undigested organic waste, to obtain a clarified broth comprising concentrated VFAs. The clarified broth and high-PHA producing bacteria are incubated to produce intracellular PHA granules in the high-PHA producing bacteria. PHA polymers are then extracted from the intracellular PHA granules.

The homogenizing is optionally done by mechanical blending using a homogenizer such as a food garburator, a mill, optionally a hammer mill and/or a grinder producing a ratio of water to organic waste of about 1:1 to 3:1 (w/w). The inoculum is optionally selected from wastewater treatment plant sludge, animal manure, and/or sediments; optionally wherein the inoculum comprises at least 10% (w/w) of the total solid content in the inoculated feedstock. The incubating of the inoculated feedstock is typically done under pH conditions of 5-9, optionally 5-6, or 6-7, or 7-8, or 8-9, temperature conditions of 35-55° C., optionally 35-40° C., or 43-47° C., or 50-55° C. and oxygen reduction potential (ORP) conditions of 0 to −300 mV, optionally −100 to −200 mV. The incubating of the inoculated feedstock can also be done with uncontrolled ORP, where the ORP varies from 0 to −900 mV. The post-incubation filtration step is required to remove all suspended acidogenic bacteria and suspended solids from the fermentation broth, prior to feeding this VFA-rich media to PHA-producing bacteria. This filtration step optionally comprises coarse filtration such as filter press and fine filtration such as gravity filtration and or filtration through a cross-flow microfiltration membrane. In an embodiment, the filtering step comprises gravity filtration, filtration through a cross-flow microfiltration membrane, or dead-end filtration, optionally further comprises adding a flocculant to the fermentation broth.

In another embodiment, the method includes, following the homogenizing step, filtering the feedstock with a filter with a pore size between about 100 µm to about 200 µm, to adjust the feedstock to the 1:1 to 3:1 (w/w) water to organic waste ratio prior to incubation. Optionally, following the incubating step, the method involves filtering the fermentation broth with the same filter type used prior to incubation with a pore size between about 100 µm to about 200 µm, or filtering with a rotary vacuum filter, decanter centrifuge, or filter press with cloth of pore size at least 0.5 µm or rated no lower than 0.25-0.8 cubic feet per minute (cfm) of air, to remove coarse solids, optionally further comprises adding a flocculant to the fermentation broth prior to filtering the fermentation broth. In an embodiment, filtering the fermentation broth uses a decanter centrifuge or filter press. In an embodiment, filtering the fermentation broth uses a decanter centrifuge. In an embodiment, filtering the fermentation broth uses a filter press. In a specific embodiment, following the incubating step, filtering the fermentation broth with the filter with a pore size between about 100 μm to about 200 μm, or a rotary vacuum filter, a decanter centrifuge, or filter press of pore size of at least 0.5 μm, to remove coarse solids, wherein the filtering the fermentation broth comprises gravity filtration, pressure/flowrate-driven filtration, optionally further comprises adding a flocculant to the fermentation broth prior to filtering the fermentation broth.

The methods described herein include conversion of VFAs to PHA carried out by an aerobic wild-type or genetically modified mixed culture of PHA-producing bacteria. The aerobic PHA producing bacteria may include one or more species of the following genera: *Brachymonas, Pseudomonas, Acinetobacter, Sphingomonas, Thauera, Cyclobacteriaceae*, where a mixture of such an aerobic culture is useful to convert the VFAs to PHAs.

Optionally, the method involves selecting the high-PHA producing bacteria that produce high amounts of PHA, wherein the selecting comprises feast famine incubation in order to obtain the high-PHA producing bacteria. In another embodiment, the feast famine incubation comprises incubating the high-PHA producing bacteria, obtained from an environmental sample, in the clarified broth and a first group of suitable nutrients. The environmental sample is optionally wastewater treatment plant sludge. The feast famine process optionally involves replacing a portion, optionally half or less, of a mixture of the clarified broth, the first group of suitable nutrients, and the PHA-producing bacteria about every 6-36 h, optionally about every: 6 h, 10 h, 12 h, 18 h, 24 h, 30 h, or 36 h with a fresh batch of the clarified broth and the first group of suitable nutrients. The clarified broth and the first suitable group of nutrients optionally comprise VFAs at 30-90 Cmmol/L, or optionally comprise VFAs at 30-60 mmol/L or 90-180 Cmmo/L, $NH_4Cl$, $KH_2PO_4$ and $K_2HPO_4$, and/or thiourea at 0.010 g/L, with a carbon to nitrogen molar ratio of 100:5 to 100:12 and with a carbon to phosphorus ratio of 100:0.5 to 100:2. The clarified broth optionally contains VFAs at a concentration of at least 30 Cmmol/L, or optionally VFAs at a concentration of at most 60 mmol/L. The clarified broth optionally contains an approximate VFA composition of about: 20-60% (w/v) acetic acid, 5-30% (w/v) propionic acid, and 20-60% (w/v) butyric acid. The selecting of the high-PHA producing bacteria is typically done under pH conditions of 6-9, optionally 6-7, 7-8, or 8-9 and temperature conditions of 20-40° C., optionally 20-25° C., 25-30° C., 30-35° C., or 35-40° C. The high-PHA producing bacteria is optionally combined with the clarified broth and a second group of nutrients comprise VFAs at: 30-90 Cmmol/L (C), optionally comprise of VFA concentrations of 30-240 VFA mmol/L or 90-720 Cmmol/L, $KH_2PO_4$ and $K_2HPO_4$ (P), and/or thiourea at 0.010 g/L, with a carbon to phosphorus molar ratio of 100:0.5 to 100:2. The incubating of the clarified broth, the second group of suitable nutrients and the high-PHA producing bacteria to produce intracellular PHA granules is typically done under pH conditions of 6-9, optionally 6-7 or 7-8, or 8-9, temperature conditions of 20-40° C., optionally 20-25° C., 25-30° C., 30-35° C., or 35-40° C. and incubation times of 1-24 h, optionally 1-3 h, 3-6 h, 6-9 h, 9-12 h, 12-18 h, or 18-24 h. The accumulation of PHA granules is monitored in certain embodiments, optionally by fluorescence spectroscopy analysis of a PHA producing culture. The extracting of the PHA polymers is optionally done with sequential washes for up to 3 times and lyophilization for 48 h at a temperatures of −20 to −80° C., optionally −30 to −35° C., or −35 to −40° C., or −40 to −45° C., or −45 to −50° C. The organic waste is optionally pretreated by thermal, acid, and/or enzymatic treatments. The method optionally further involves analysis of the VFA composition, optionally by gas or liquid chromatography, and the clarified broth is adjusted to achieve a desired VFA concentration.

Another aspect of the disclosure relates to an apparatus for producing polyhydroxyalkanoates (PHA) from organic waste optionally including:

a homogenizer for homogenizing the organic waste;

a VFA fermentation tank for incubating feedstock that has been inoculated with an inoculum of acidogenic fermentative bacteria, the incubator producing a fermentation broth comprising volatile fatty acids (VFAs) and undigested organic waste;

a filter system for the fermentation broth to remove the acidogenic fermentative bacteria and undigested organic waste, to obtain a clarified broth comprising concentrated VFAs;

a high-PHA producing bacteria inoculum tank; and a PHA fermentation tank for incubating the clarified broth and high-PHA producing bacteria to produce intracellular PHA granules in the high-PHA producing bacteria.

The homogenizer is optionally a food garburator, a mill, optionally a hammer mill and/or a grinder. The filter system optionally includes a fine filter and optionally a coarse filter, the fine filter having a pore size ranging from 0.2 μm to 500,000 NMWC, optionally 0.2 μm to 300,000 NMWC, and the coarse filter having a 100-200 micron pore size. The fine filter is optionally a multiple cartridge membrane filter. The apparatus optionally includes an air-operated double diaphragm pump to convey the feedstock from the homogenizer or pretreatment vessel into the VFA fermentation tank. The VFA fermentation tank is optionally a semi-continuous stirred tank reactor. The high-PHA producing bacteria inoculum tank is optionally a semi-continuous stirred tank or agitated reactor.

BRIEF DESCRIPTION OF THE DRAWINGS

Reference is made in the description of various embodiments to the accompanying drawings, in which:

FIG. 6A is a spectra of commercial P3HB. FIG. 6B is extracted PHA.

FIGS. 14A-14C show a graphical representation of VFA production from acidogenic fermentation of organic waste at varying pH, temperatures and organic loading rates at an incubation time of 3 days. FIG. 14A is a graph of varying pH, temperatures at 5% organic loading rate, FIG. 14B is a graph of varying pH, temperatures at 10% organic loading rate, and FIG. 14C is a graph of varying pH, temperatures at 15% organic loading rate.

FIG. 15A is a graph on the effect of temperature and pH on VFA yield at an incubation time of 3 days, FIG. 15B is a graph on the effect of temperature and organic loading rate on VFA yield at an incubation time of 3 days, and FIG. 15C is a graph on the effect of organic loading rate and pH on VFA yield at an incubation time of 3 days.

FIG. 16A is a graph on the effect of 30 mmol/L VFA at varying pH on PHA concentration over time, FIG. 16B is a graph on the effect of 45 mmol/L VFA at varying pH on PHA concentration over time, FIG. 16C is a graph on the effect of 60 mmol/L VFA at varying pH on PHA concentration over time, FIG. 16D is a graph on the effect of 30 mmol/L VFA at varying pH on normalized cell density over time, FIG. 16E is a graph on the effect of 45 mmol/L VFA at varying pH on normalized cell density over time, and FIG. 16F is a graph on the effect of 60 mmol/L VFA at varying pH on normalized cell density over time.

DETAILED DESCRIPTION

1. Definitions

The term "organic waste" as used herein refers to biodegradable portion of municipal, agricultural, and industrial waste, including solid waste, that contain organic matter that is useful for producing volatile fatty acids (VFA) by bacteria. For example, the organic waste can be from any restaurant, grocery store, household kitchen, cafeteria, food retailer, or food processing facility. The organic waste includes food, such as food or ingredients disposed of by the restaurant, for example unused, spoiled or leftover food or ingredients, or the grocery store, for example fruits, vegetables, meats, dairy products and processed foods.

Figure 8:
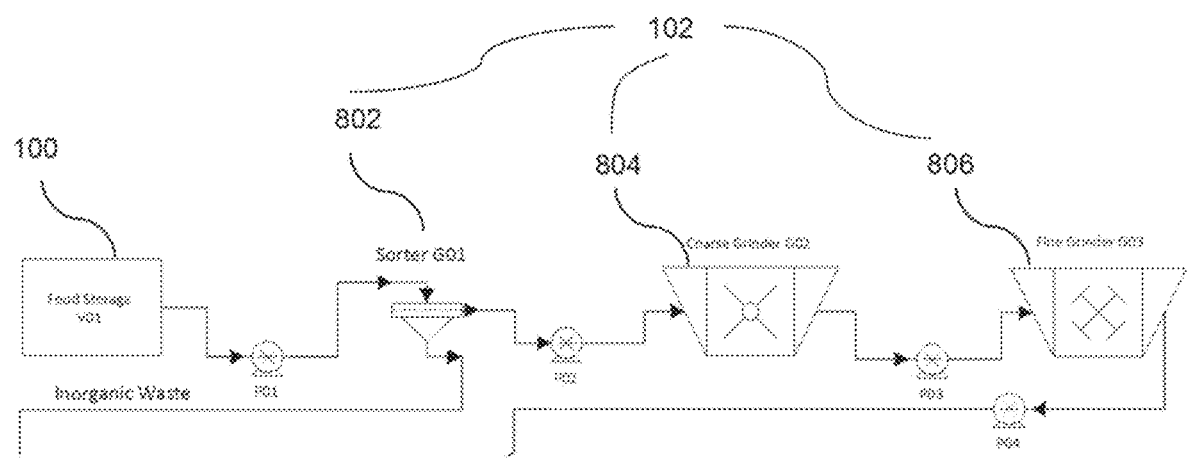
FIG. 8 is a detailed block flow diagram of organic waste reception, sorting, and grinding.

The term "homogenize" or a derivative thereof as used herein refers to grinding and blending process of organic waste into a homogeneous mixture of fine and coarse particles. Homogenization can be carried out in the presence of a liquid, for example, water. Homogenization can be carried out in a single step (Refer to 102 in FIG. 1) or include separate coarse and fine grinding (Refer to 804/806 in FIG. 8). For example, combined operation units 804 and 806 shown in FIG. 8 represent the homogenization operation units 102 in FIG. 1.

The term "volatile fatty acid" or "VFA" as used herein refers to fatty acids with less than six carbon atoms. For example, VFA includes, but not limited to formic acid, acetic acid, propionic acid, butyric acid, isobutyric acid, valeric acid, and isovaleric acid. The VFA described herein are useful source materials to be converted to PHA by bacteria.

The term "polyhydroxyalkanoate", "PHA", or "PHA polymer" as used herein refers to polyesters that can be produced by microorganisms, including bacteria, through fermentation of a carbon source, for example, sugar, lipids, or fatty acids. PHA is biodegradable and is useful in the production of bioplastics.

The term "acidogenic fermentative bacteria" as used herein refers genetically modified bacteria or wild-type bacteria that are naturally occurring with characteristics of moderately thermophilic, anaerobic bacteria, which are capable of converting simple monomers into VFA. Moderate thermophiles are bacteria that has an optimum growth temperature between 40-55 degree celsius. These bacteria are useful in the process of converting organic waste to VFA.

The term "feedstock" as used herein refers to a basic material that is used to produce a product. For example, a feedstock can be obtained by homogenizing organic waste. The feedstock can have a water to organic waste ratio of about 1:1 to 3:1 (w/w). For example, a feedstock can be used to produce volatile fatty acids by bacteria.

The term "organic loading rate" as used herein refers to the percentage of organic waste introduced into a culture for fermentation. The mass of organic waste is in reference to its dry mass, i.e. where the organic waste has no or is substantially free of water content. As such, organic loading rate is represented by the formula of:

Dry mass of organic waste/total mass of a culture (i.e. liquid mass+solute mass+Dry mass of organic waste)*100%

The term "filtrating" or a derivative thereof as used herein refers to a process of separating solids from fluids by adding a medium through which only the fluid can pass, for example, removing suspended solids and acidogenic bacteria from a fermentation broth, prior to feeding it to the PHA-producing bacteria. This may include a coarse filtration step (Refer to operation unit 200 and/or 202 in FIG. 10) and/or followed by a fine filtration step (Refer to operation unit 204/206 in FIG. 10). The coarse filtration step is used to remove solids as small as 0.5 μm, and may include the use of filter press, decanter centrifuge, rotary drum vacuum filter (RVDF), screw press or other pressure-induced dead-end filtration systems, or flocculation tanks and other gravity-based separation systems. The terms filter press and plate press are used interchangeably. The fine filtration step refers to a system that can filter in the range of 0.22 μm to as low as 300,000 NMWC and can remove fine particle sized suspended solids and bacteria. This can be achieved with the use of hollow fiber or tubular membrane cross-flow filtration systems, or variations of microfiltration and ultrafiltration membranes.

The term "cross-flow filtration" as used herein refers to a filtration technique in which the majority of the feed flow travels tangentially across the surface of the filter, rather than into the filter. During cross-flow filtration, filter cake that can blind the filter is substantially washed away during the filtration process, thereby the length of time that a filter unit can be operational is increased. Retentate cake is the holdup volume left over in the feed tank that is highly concentrated in solids that cannot be filtered and is discarded. Under batch mode, retentate may be as much as 10% of the initial volume in the feed tank. Cross-flow filtration can be carried out under continuous mode. Cross-flow filtration is useful for obtaining materials from fermentation broth.

The term "environmental sample" as used herein refers to a source of PHA-producing bacteria, preferably high PHA-producing bacteria. The environmental sample can be wastewater treatment plant sludge, animal manure, and/or sediments. Sediments refer to mineral sediments such as soil or sands that contain biomass. An environmental sample is useful for selecting high-PHA producing bacteria, for example, through feast famine incubation.

The term "wastewater treatment plant sludge" as used herein refers to the residual, semi-solid material that is produced as a by-product during wastewater treatment of industrial, municipal or other wastewater that contains organic matter. For example, municipal wastewater sludge may contain human feces and/or organic garbage.

The term "granule" as used herein relating to PHA refers to the form of PHA accumulated inside bacteria. PHA is stored inside bacteria as discrete water-insoluble intracellular granules. PHA granules can be extracted from bacteria by the methods described herein.

The term "mmol/L" as used herein refers to a measure of the concentration of a solute in a solution in the unit of mmol of the solute per litre solution.

The term "Cmmol/L" as used herein refers to a measure of the concentration of a solute in a solution in the unit of mmol of carbon per litre solution.

The term "VFA mmol/L" as used herein refers to a measure of the concentration of total VFA in a solution in the unit of mmol of VFA per litre solution.

The term "permeate" as used herein refers to clarified broth, for example, fermentation broth, that passes through a membrane, for example a filter membrane, for example, a hollow-fibre membrane or a tubular membrane.

The term "cloudy" as used herein refers to a change of the solution appearance, from transparent to white translucent appearance. For example, for extracting PHA from bacteria, sequential surfactant-hypochlorite digestion or chloroform-hypochlorite dispersion may be used, The phrase "substantially free" as used herein is used to refer to the complete or near complete lack of an action, characteristic, property, state, structure, item, or result. For example, a composition or organic waste that is "substantially free of" water would either completely lack water, or so nearly completely lack water that the effect would be the same as if it completely lacked water. In other words, a composition that is "substantially free of" an element may still actually contain such item as long as there is no measurable effect thereof. For example, a composition or organic waste that is substantially free of an ingredient or element comprises less than about 1% by wt or less than about 1% vol/vol of the ingredient or element in the composition.

The term (w/v) as used herein refers to a measure of the concentration of a solution or mixture obtained by dividing the mass or weight of the solute by the volume of the solution or mixture.

The term (w/w) as used herein refers to a measure of the concentration of a solution or mixture obtained by dividing the mass or weight of the solute by the weight of the solution or mixture.

The term "operation" as used herein refers to a method that describes a technique or an equipment type, a mode that refers to continuous or batch operation modes, an operation unit that refers to process blocks in the block flow diagram, or an operation, time between turning a specified equipment ON or OFF.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this specification and the appended claims, the singular forms "a", "an" and "the" include plural references unless the content clearly dictates otherwise. It should also be noted that the term "or" is generally employed in its sense including "and/or" unless the content clearly dictates otherwise.

The recitation of numerical ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about".

The definitions and embodiments described in particular sections are intended to be applicable to other embodiments herein described for which they are suitable as would be understood by a person skilled in the art.

2. Methods and Apparatus

Although the apparatus and methods may relate to the production of PHA from commercial kitchen organic waste, the apparatuses and methods described herein may be used for the production of PHA from organic waste from any restaurant, household kitchen, cafeteria, food retailer, or food processing facility. The organic waste comprises food, such as food or ingredients disposed of by the restaurant, for example unused, spoiled or leftover food or ingredients, or the grocery store, for example fruits, vegetables, meats, dairy products and processed foods.

An aspect of the present disclosure includes a method for producing PHA from organic waste. The method comprises homogenizing organic waste to obtain a feedstock that has a 1:1 to 3:1 (w/w) water to organic waste ratio, inoculating the feedstock with an inoculum of acidogenic fermentative bacteria in order to obtain an inoculated feedstock, incubating the inoculated feedstock for 5 to 10 days, optionally 3 to 10 days, optionally 7 days, optionally 3 days, to obtain a fermentation broth, wherein the fermentation broth comprises VFAs and undigested organic waste, filtering the fermentation broth with a filter with a pore size ranging from 0.2 μm to 500,000 NMWC, optionally 0.22 μm to 300,000 NMWC, to remove the acidogenic fermentative bacteria and undigested organic waste, to obtain a clarified broth comprising concentrated VFAs, incubating the clarified broth and high-PHA producing bacteria to produce intracellular PHA granules in the high-PHA producing bacteria and extracting PHA polymers from the intracellular PHA granules.

An accelerated PHA polymer production method as described herein can also be employed. The accelerated PHA polymer production method can be used with various acidogenic fermentative bacteria and high PHA-producing bacteria. Conventionally, the step of producing VFAs from organic waste takes at least 7-10 days. In the method described herein using the disclosed pH, temperature, organic loading rate and/or oxygen reduction potential (see Examples), the production of VFAs from organic waste can be carried out in as few as 3 days. When combining this accelerated step of producing of VFAs from organic waste with the second fermentation step of producing PHA from VFAs, cell harvesting, lyophilization, and extraction, the process of producing PHA from organic waste can be done in between 7-8 days. In an embodiment, the method described herein for producing VFA comprises incubating the inoculated feedstock at about pH 5-9, optionally about 5-6, or 6-7, or 7-8, or 8-9, temperature at about 35-55° C., optionally 35-40° C., or 43-47° C., or 50-55° C., organic loading rate at about 5-15%, optionally about 9-15%, and optionally oxygen reduction potential (ORP) conditions of 0 to −300 mV, optionally −100 to −200 mV and an uncontrollable ORP of 0--900 mV. In an embodiment, the method described herein comprises producing VFAs from organic waste in 3-5 days, preferably 3 days. In an embodiment, the method described herein comprises producing PHA polymers from organic waste in less than 10, 9, 8, or 7 days, preferably less than 8 or 7 days.

Figure 1:
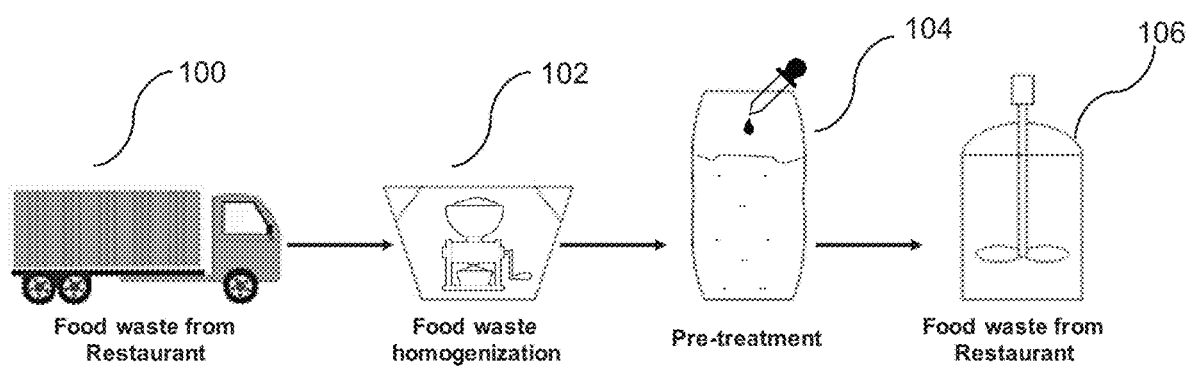
FIG. 1 is a process flow diagram for food waste to VFA fermentation.

Reference is made to FIG. 1, which shows an exemplary first embodiment of the method. In an embodiment, waste storage 100 (see also operation unit 100 from FIG. 1 and/or FIG. 8) is transported to a centralized facility where it may be sorted to remove non-digestible wastes, optionally using manual sorting or any other standard sorting mechanisms capable of removing non-digestible plastics and metals (Refer to 802 in FIG. 8), and then is homogenized in a homogenizer (also refers to operation units 804 and 806 from FIG. 8). Sorting may include several other systems such as magnetic belts that separate metals from organics, trommels (big sieve drums). Sorting technology still needs much improvement and manual intervention is almost always necessary. Sorting and homogenization operation units combined, for example, refers to 102 in FIG. 1 and FIG. 8. Herein any reference made to homogenization process also refers to, for example, the operation unit 804 and 806 from FIG. 8. Organic waste homogenization optionally involves dry or wet mechanical particle reduction. In the latter case, organic waste mass and optionally added water is controlled before and after particle reduction to meet organic loading rate thresholds of 7-15% (w/w) of total solids. The loading thresholds typically vary depending on the homogenization equipment. Homogenization can be performed optionally by mechanical blending in one or multiple steps. For example, a homogenization process referring to 804 in FIG. 8 such as a hammer mill or other type of mill is useful for the bulk raw material, and subsequently finer grinding may be performed with a garburator or other grinding methods. Other appropriate equipment for organic waste homogenization is also useful. Additional mechanical disruption is optionally used to further reduce particle size. This process optionally involves filtration of food solids and recirculation of the permeate in order to obtain a desired water to organic waste ratio of about 1:1 to 3:1 (w/w). In an embodiment, the ratio of water to organic waste ratio is about 1:1 to 3:1 (w/w). In an embodiment, the ratio of water to organic waste ratio is about 1:1 (w/w). The range can be any range between 1:1 to 3:1 (w/w), including for example any 0.01 increment such as a range of 1.01 to 1 or 2.99 to 1 (w/w). Similarly, a specific ratio can be any 0.1 increment between and including 1:1 and 3:1 (w/w). Filtration is optionally done by a 100 μm to 200 μm cut-off sieve filter. VFA fermentation equipment, as well as filtration and PHA production equipment, can be engineered for scalability in order to accommodate smaller and larger scales of PHA production.

Figure 9:
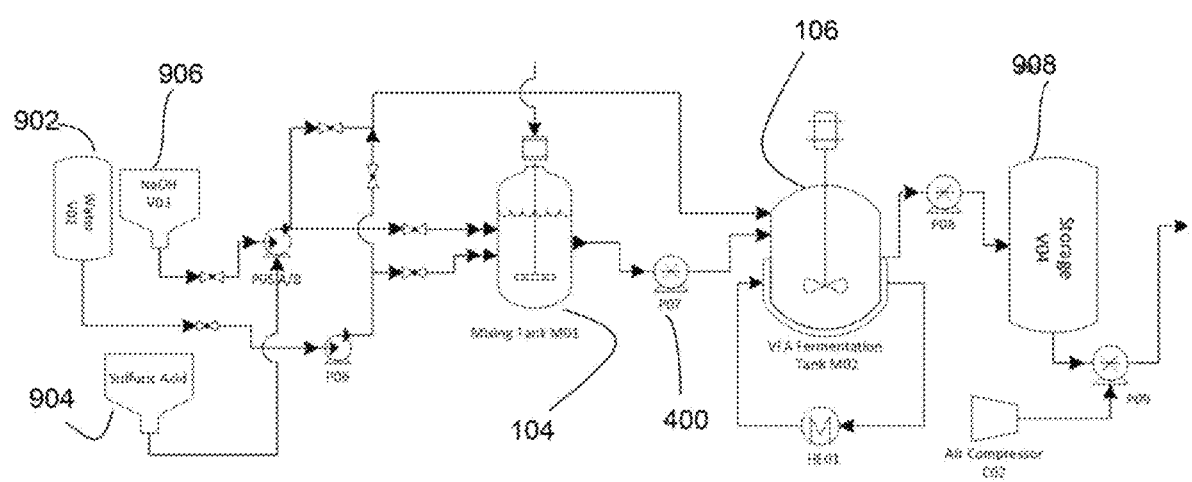
FIG. 9 is a detailed block flow diagram of organic waste chemical pretreatment and anaerobic digestion.

In an aspect, feedstock is pretreated in a pretreatment vessel, for example, pretreatment vessel 104 in FIG. 9, to improve the yield of VFAs during acidogenic fermentation, which is carried out in, for example, a fermentation tank 106 (FIG. 9). Pretreatment method relevant to VFA fermentation disclosed herein refers to, for example, operation unit 104 in FIG. 9. Pretreatments optionally include thermal, acid, and/or enzymatic treatments. The goal of pretreatment is to increase the solubility, and thus bioavailability, of organic matter in the feedstock. Thermal treatment typically involves heating the food waste to a temperature of 70-200° C. for a period of time ranging from 30 minutes to several hours, or up to several days, optionally 2 days. Acid treatment typically involves lowering the pH of the feedstock to about 1-3 by the addition of acid in order to increase hydrolysis of the organic matter. Through hydrolysis, enzymatic treatment helps to break down organic polymers (for example polysaccharides, lipids, proteins) in the organic waste into their constituent parts, for example sugars, fatty acids, and amino acids. Enzymatic treatment can be done using enzymes such as carbohydrases, proteases, and lipases. In an embodiment, pretreatment comprises thermal, acid and/or enzymatic treatment. In an embodiment, pretreatment comprises thermal treatment. In an embodiment, thermal treatment comprises heating a feedstock at about 70-200° C. for about 30 minutes to at most about 18 h, optionally at most about 17, 16, 15, 14, 13, 12, 11, 10, 9, 8, 7, 6, 5, 4, or 3 h. In an embodiment, pretreatment comprise acid treatment. In an embodiment, acid treatment comprises maintaining a feedstock at pH about 1-3, optionally, about 3, 2.5, 2, 1.5, or 1 for about 30 minutes to at most about 18 h, optionally at most about 17, 16, 15, 14, 13, 12, 11, 10, 9, 8, 7, 6, 5, 4, or 3 h. In an embodiment, pretreatment comprises enzymatic treatment about 30 minutes to at most about 18 h, optionally at most about 17, 16, 15, 14, 13, 12, 11, 10, 9, 8, 7, 6, 5, 4, or 3 h. In an embodiment, enzymatic treatment comprises adding an enzyme to a feedstock. In an embodiment, the enzyme is a carbohydrase, protease, and/or lipase.

Figure 4:
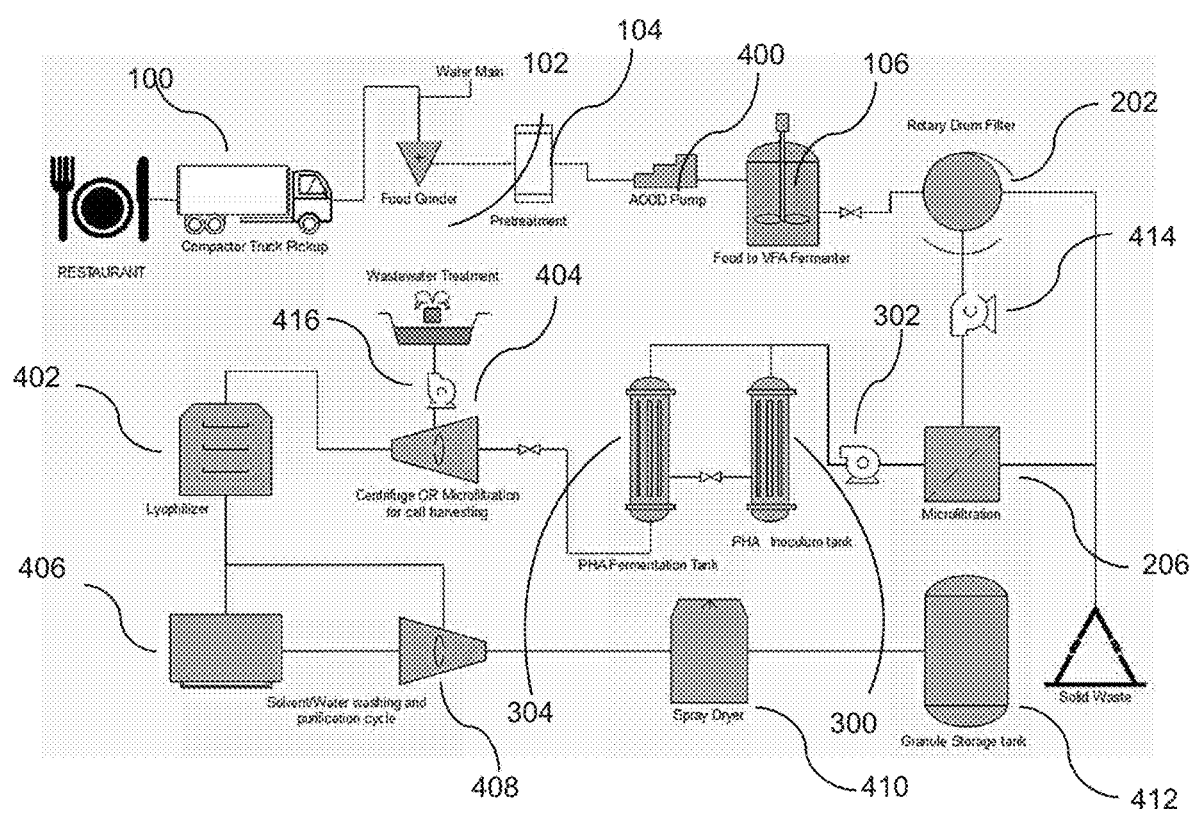
FIG. 4 is a process flow diagram for industrial production of PHA bioplastics from organic waste.

In an aspect, the feedstock is then conveyed into equipment for acidogenic fermentation 106 (FIG. 9) optionally using a controllable air-operated double diaphragm pump (AODD) (refer to operation unit 400) as seen in FIG. 4. & FIG. 9, or other mass transfer systems capable of handling liquids with high solids concentration, optionally positive-displacement pumps. AODD is a pump that uses compressed air to operate which slows down and shuts off when desired loading pressure is reached, and then it turns on again when pressure decreases, without the need for electronic automation. Conveying the feedstock in this manner into the equipment for acidogenic fermentation 106 can be advantageous over an uncontrolled transfer as it may provide greater control over the VFA production process. In an embodiment, a controllable air-operated double diaphragm pump (AODD) or a positive displacement pump conveys a feedstock from a homogenizer or pretreatment vessel into a VFA fermentation tank. In an embodiment, the VFA fermentation tank is a stirred tank reactor. In an embodiment, the stirred tank reactor is in semi-continuous mode or batch mode. In an embodiment, the VFA fermentation tank is a semi-continuous or batch mode stirred tank reactor.

In an aspect, the equipment used for acidogenic fermentation involves a suspended growth semi-continuous stirred tank reactor. For example, VFA fermentation tank also refers to operation unit 106 shown in the FIG. 9. Tanks are readily scaled on mixing tip speed which may be controlled in a range of 3-6 m/s, optionally 4.5 m/s. The impellers installed in the fermentation tank includes but not limited to use of marine propellers, pitched-blade impellers, or hydrofoil impellers for mechanical agitation, which is not limited to top entry systems. One tank could have more than one type of impeller or propeller in different positions. A tank can also have a certain number of one type of impeller, for example, a centered shaft with 3-marine props on it. In an embodiment, the tanks comprises marine propellers, pitched-blade impellers, and/or hydrofoil impellers. The tanks may be aerated through controlled air sparging, and dissolved oxygen levels may be controlled. Temperature may be controlled through direct ON/OFF heating elements. Alternatively heating may be controlled through a jacket heat exchanger system. Concentrated sodium hydroxide (NaOH) (Refer to 906 in FIG. 9) may be added through an appropriate pump to control pH. In an embodiment, NaOH is added to a pump to control pH.

In an embodiment, the feedstock is inoculated with acidogenic fermentative bacteria in the fermentation tank 106, wherein the inoculum is selected from wastewater treatment plant sludge, animal manure, and/or sediments; optionally wherein the inoculum comprises at least 10% (w/w) of the total solid content in the inoculated feedstock.

In an embodiment, the inoculated feedstock is incubated in the fermentation tank 10 under conditions as shown in FIGS. 14A-14C, 15A, 15B, and 15C. In an embodiment, the inoculated feedstock is incubated in a fermentation tank under pH conditions of 5-9, optionally 5-6, 6-7, 7-8, or 8-9, temperature conditions of 35-55° C., optionally 35-40° C., 40-43° C., 40-42° C., 43-47° C., or 50-55° C., organic loading rate of 5-20% (w/w), optionally 5-10%, 10-15%, or 15-20%, and ORP conditions of 0 to −900 mV, −300 mV, or −200 mV, to obtain a fermentation broth. In a specific embodiment, the inoculated feedstock is incubated in a fermentation tank under pH 7-8, temperature at 40-42° C., and organic loading rate of 9-15%, and optionally 0 to −900 mV, −300 mV, or −200 mV, to obtain a fermentation broth.

In an embodiment, following the incubation period of 5 to 10 days, optionally 3 to 10 days, optionally 7 days, optionally 3 days, the fermentation broth is filtered. In an embodiment, the filtering can optionally be done by gravity filtration and/or filtration through a cross-flow microfiltration or ultrafiltration membrane. In an embodiment, filtering step comprises gravity filtration, pressure/flowrate-driven filtration through a cross-flow microfiltration membrane, or dead-end filtration.

Figure 2:
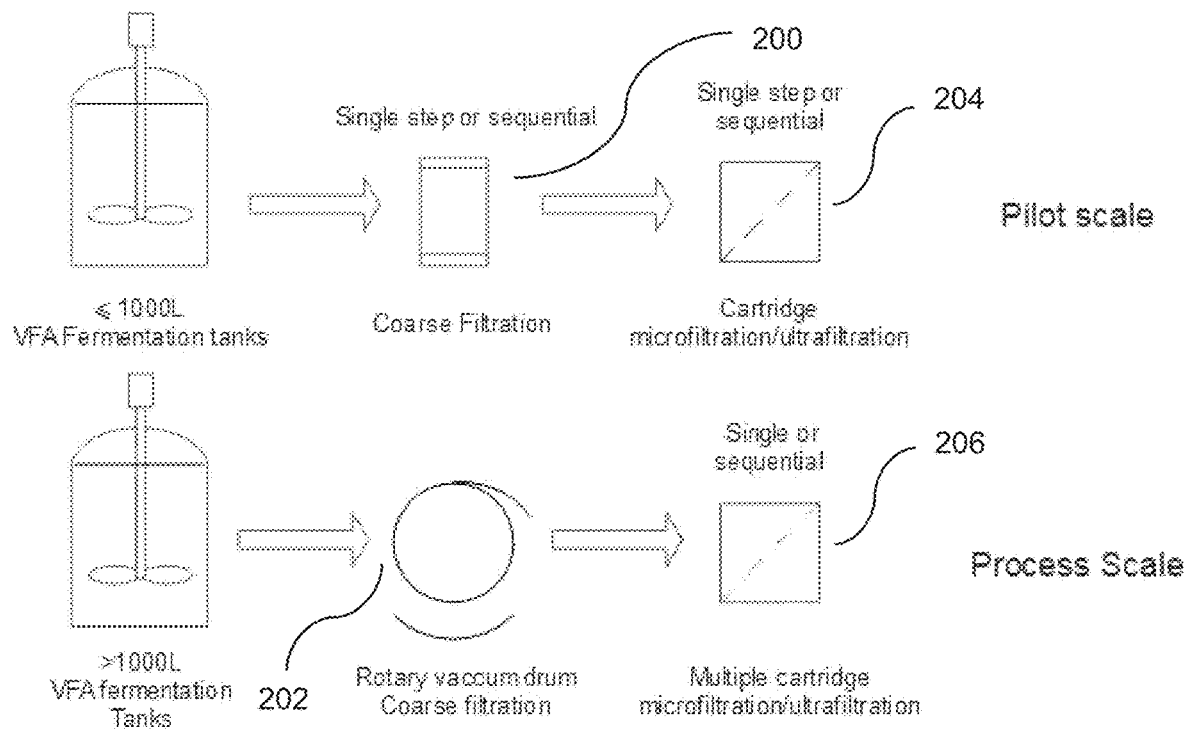
FIG. 2 is a process flow diagram of acidogenic fermentation broth filtration and pretreatment for PHA-producing bacteria.
Figure 10:
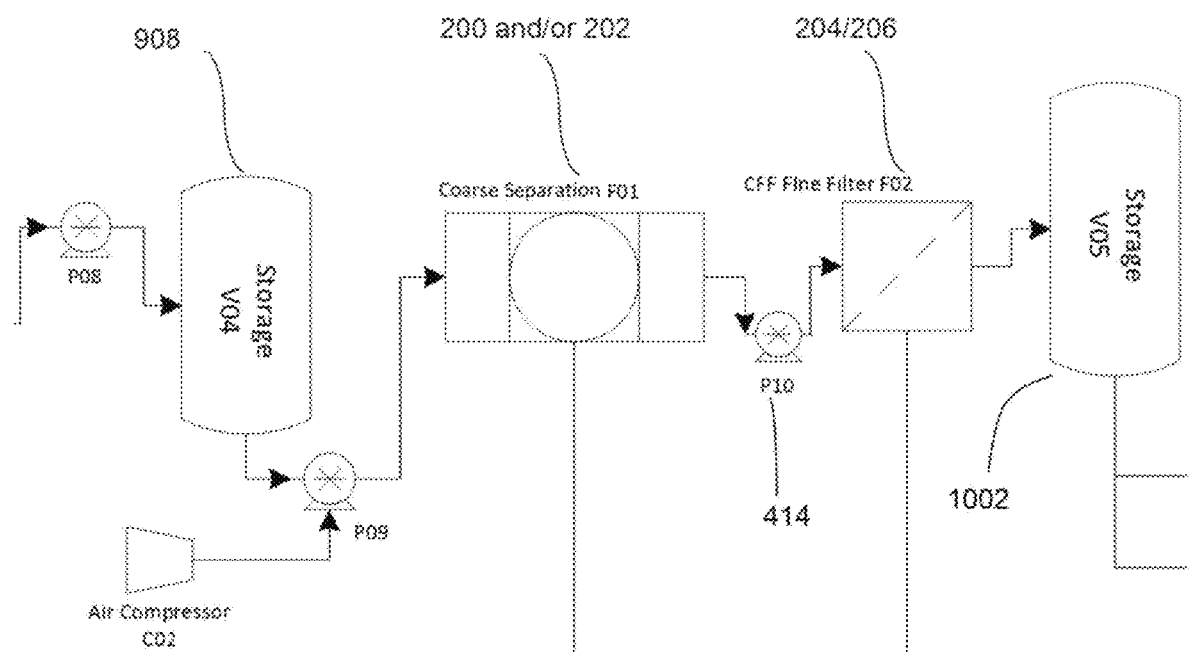
FIG. 10 is a detailed block flow diagram of fermentation broth solids separation process, including coarse filtration and micro/ultrafiltration. Where a filter press is used, coarse filtration cut-off may be as low as 0.5 micron. A decanter centrifuge may also be used.

In an aspect, coarse filtration (also known as coarse solids separation) described herein refers to, for example, the operation unit 200 and/or 202 shown in FIG. 10. Coarse filtration may include pressure-induced filtration systems, such as for example use of a filter press, rotary drum vacuum filter, or screw press. Coarse filtration may also include gravity based systems such as use of decanter centrifuge, or flocculation settling tanks. As also exemplified in FIG. 2, filtration may comprise a filtration system of two steps although it is also possible to filter in a single step. The first step is optional and involves a coarse filtration wherein the fermentation broth is filtered through a coarse filter 200 in FIG. 2 with a pore size that may be as fine as 100 μm to 200 μm cut-off, at a smaller scale or optionally through a rotary vacuum drum 202 in FIG. 2 at a larger process scale. Coarse solids separation may also be achieved with a decanter centrifuge, or filter plate press of pore size as low as 0.5 μm cut-off. In an embodiment, the coarse filtration is performed to remove coarse solids from the fermentation broth, optionally further comprises adding a flocculant to the fermentation broth prior to filtering the fermentation broth. In an embodiment, coarse filtration comprises a pressure-induced filtration system or a gravity-based system. In an embodiment, the pressure-induced filtration system is a filter press, rotary drum vacuum filter, or screw press. In an embodiment, gravity-based system is a decanter centrifuge, or a flocculation settling tank. All coarse filtration methods described herein may involve the use of flocculation. The addition of flocculants to fermentation broth can increase the average particle size making microfiltration more efficient. Flocculants can be positively or negatively charged, and positively charged flocculants such as cationic polymer typically functions better because cells, for example bacterial cells, are generally negatively charged. In an embodiment, coarse filtration comprises flocculation. In an embodiment, flocculation comprises addition of a flocculant. In an embodiment, the flocculant comprises cationic polymer. In an embodiment, the cationic polymer comprise cationic polyacrylamide polymer. The stirred tank mixer may operate under batch, semi-continuous or continuous mode depending on desired loading in the coarse filtration step, allowing for hydraulic residence time (HRT) to be higher than the stirred tank mixer's mixing time. After mixing, under batch mode, the entire contents (i.e. fermentation broth mixed with flocculant) are drained and fed to the coarse filters. Under semi-continuous mode, a portion of the mixed content is drained at set intervals. Under continuous mode, where there is a constant flow in and out of stirred tank mixer. In an embodiment, flocculation comprises operating stirred tank mixer under batch, semi-continuous or continuous mode.

In an embodiment, the flocculated fermentation broth is then transferred into one of the coarse filtration systems, optionally pressure-induced dead-end systems such as filter press, rotary drum vacuum filter (RVDF), or screw press, or gravity-based separation systems such as decanter centrifuge. In an embodiment, the flocculated fermentation broth is transferred into a coarse filtration system, optionally pressure-induced dead-end systems, optionally a filter press, rotary drum vacuum filter (RVDF), or screw press, or a gravity-based separation systems, optionally a decanter centrifuge. In an embodiment, the coarse filtration system is pressure-induced dead-end filtration system or gravity-based separation system. In an embodiment, the pressure-induced dead-end filtration system is filter press, decanter centrifuge, rotary drum vacuum filter (RVDF), or screw press. In an embodiment, the filtration methods described herein do not include flocculation.

In an embodiment, post acidogenic fermentation, filtration is used to remove all suspended acidogenic fermentative bacteria and suspended solids from the fermentation broth, prior to feeding this VFA-rich media to PHA-producing bacteria. In an embodiment, sequential separation must be used for successful and complete bacteria and biosolids removal. In an embodiment, coarse filtration methods described herein comprises flocculation.

In an embodiment, fermentation broth is loaded into a mixing tank, optionally a mechanically stirred tank. In an embodiment, a flocculant is added to the mixing tank by a dosing pump. In an embodiment, the flocculant is cationic polymer flocculant. In an embodiment, the cationic polymer flocculant is a cationic polyacrylamide polymer flocculant. In an embodiment, flocculant is introduced into a stirred tank mixer containing fermentation broth. In an embodiment, stirred tank mixer is in batch or semi-continuous mode. In embodiment, stirred tank mixer provides for hydraulic residence time (HRT) to be higher than the mixer's mixing time. In an embodiment, the flocculated fermentation broth is transferred into a coarse filtration systems, optionally a filter press, a decanter centrifuge, a rotary drum vacuum filter (RVDF), a screw press, a pressure-induced dead-end filtration system, or a gravity-based separation system.

In an embodiment, the coarse filtration method described herein uses a filter press. In an embodiment, then fermentation broth is loaded into a filter press using a controllable air-operated-double-diaphragm pump (AODD) or positive-displacement pump. In an embodiment, the filter press is in a batch or continuous mode, with residence times of 1 to 6 h. In an embodiment, the filter press cloth used is optionally rated in air permeation, as low as 0.25-0.8 cfm, or equivalent cloth pore size as low as 0.5 µm. Larger pore size cloth may be used, at the expense of fine filtration performance and costs. In this manner, cloth pore size may be as high as 1000-50 µm. Cloth material is optionally nylon plastic with silicone sealant. In an embodiment, cloth does not include sealant or use different materials. Plate and frame type filter press refers to an assembly of flat plates (plate) alternating with hollow plates (frame) containing the filter cloth. Recessed plate type filter press refers to using a single repeated type of concave hollow plates that also contains the filter cloth. In an embodiment, filter press is plate and frame type or recessed-plate type, optionally gasketed recessed polypropylene plates are used. In an embodiment, filter press is plate and frame type. In an embodiment, filter press is recessed-plate type. In an embodiment, filter press is a gasketed recessed polypropylene plate. Alternatively, plates may not use gaskets or be recessed, at the expense of leakage. Alternatively, stainless steel plates may be used. In an embodiment, filter press comprises stainless steel plates. The filter press may be closed via hydraulic system, electric, or manually. In an embodiment, filter press is closed via hydraulic system, electric, or manually. In an embodiment, the fermentation broth is initially loaded into the press at 10-35 psi internal filter press pressure. In an embodiment, once the press is full, the pressure is increased to 35-65 psi for at least 1 hour HRT. In an embodiment, as the filtrate flow rate drops, the press pressure is increased to 75 psi, 90 psi, and at most 110 psi. In an embodiment, maximum HRT for fermentation broth is 3 h-6 h. In an embodiment, the filter press is air blowdown to dry filter cake. In an embodiment, the method described herein comprises filter press closing, press opening, loading, pressurizing and hold pressures, for 5-10 min, at about or at most 220 psi. In an embodiment, filtrate is collected and stored in a cold storage tank of temperature as low as 4° C. In an embodiment, filtrated fermentation broth is immediately proceeds to the fine filtration stage following coarse filtration. In an embodiment, the filter press is opened and solids are recovered manually by an operator or be automated. In an embodiment, the filter press is under air-only operation to clean filter cloths.

In an embodiment, the fermentation broth flows into a decanter centrifuge, operated either as a batch or continuous mode. In an embodiment, the decanter centrifuge operated in force ranges between 1000×g and 4000×g. Solids are disposed of and fermentation broth is forwarded to the filter press stage described above. In an embodiment, post decanter centrifuge operation, the filter press is expected to have lower HRT and higher filtrate flow rate as compared to filtering fermentation broth by filter press alone. Similarly, to the decanter centrifuge, several other common gravity-based dewatering systems may be used for coarse filtration. This includes but is not limited to flocculation settling tanks, variations of sequential batch reactors with supernatant collection, or disk stack centrifuges.

In an embodiment, a RVDF is used in sequence preceding a filter press or as a standalone. In an embodiment, The RVDF is operated under semi-continuous mode, where filter cake is continuously scraped off the RVDF's membrane surface. In an embodiment, filtrate is loaded into a filter press or into cold storage at about 4° C. for fine filtration.

In an embodiment, coarse filtration comprises a hollow fiber or tubular membrane cross-flow filtration. In an embodiment, initially after coarse filtration, the fermentation broth filtrate is circulated at constant flow rate through a hollow fiber membrane cartridge of pore size 0.22 µm-300,000 NMWC. In an embodiment, the fine filtration system is arranged into any number of cartridges in parallel. In an embodiment, each of the cartridges used are 30-60 cm length, 0.5-1.5 mm lumen diameter, and made of polysulfone material. In an embodiment, permeate is defined as clarified broth that passes through the hollow fiber or tubular membrane and is collected in cold storage at about 4° C. to be fed to PHA-producing bacteria downstream. In an embodiment, retentate is defined as broth that is not filtered and circulates into the fine filtration system's feed tank. In an embodiment, the permeate is recovered and the retentate is concentrated. In an embodiment, under batch mode, as much as 10% of initial broth volume is discarded as concentrated retentate. In an embodiment, semi-continuous and continuous mode yields higher retentate recovery.

In an aspect, microfiltration and ultrafiltration membranes described herein includes variations. Variations may include several common water purification membrane systems either in cross flow or dead-end flow configuration. Those may include mechanisms such as but not limited to reverse osmosis systems, dead-end tubular membrane cartridges, and electrodialysis system.

In an embodiment, coarse filtration method described herein comprises use of filter press. In an embodiment, the fermentation broth is loaded into a filter press, using a controllable air-operated-double-diaphragm pump (AODD) or positive-displacement pump. Using an AODD pump here allows for easy control over the filter press operating pressure and causes a significant improvement in filtration efficiency, by allowing us to slowly ramp up pressure in the press (15 psi loading, 50, 75, 100, etc.). In an embodiment, the filter press is used as a batch or continuous mode. In an embodiment, residence times for batch or continuous mode is between about 1 and 6 hrs. In an embodiment, the filter press comprises a filter press cloth. In an embodiment, the filter press cloth is at least about 0.25-0.8 cfm, or at least about 0.5 µm, or about at most 1000-50 µm pore size. In an embodiment, the filter press cloth comprises nylon plastic and/or silicone sealant. In an embodiment, the filter press is plate and frame type, or recessed-plate type. In an embodiment, the filter press is a gasketed recessed polypropylene plate or a stainless steel plate. In an embodiment, the closing of filter press is hydraulic, electrical or manual. In an embodiment, the filter press is hydraulic closing filter press. In an embodiment, the fermentation broth is loaded into the filter press at about 10-35 psi internal filter press pressure. In an embodiment, when the press is full, the pressure is increased to about 35-65 psi for at least about 1 hour hydraulic residence time (HRT). In an embodiment, the press pressure is increased to about 75 psi, about 90 psi, and at most about 110 psi. In an embodiment, the HRT is most about 110 psi for about 3-6 hrs. The filter press can be air blowdown in order to dry the filter cake. In an embodiment, the filter press is air blown to dry the filter cake. In an embodiment, the filter press increased pressure from 100 psi to 220 psi for about 5-10 min, thereby increasing filtrate yield. In an embodiment, the filtrate is collected and stored in a cold storage tank about at least 4° C. Cold storage of filtrate is not necessary if the fermentation broth immediately proceeds to the fine filtration stage. Fine Filtration is shown as operation unit 204/206 in the FIG. 10. In an embodiment, the press is opened and solids is recovered manually by an operator. The press may operate with air only to clean of the filter cloths.

In an embodiment, the fermentation broth flows into a decanter centrifuge. In an embodiment, the decanter centrifuge is in batch or continuous mode. In an embodiment, the decanter centrifuge is maintained at a force range between about 1000×g and 4000×g. In an embodiment, solids are disposed of and fermentation broth is forwarded to the filter pressing step described herein. In an embodiment, the filter press has lower HRT and higher filtrate flow rate. In an embodiment, coarse filtrating is conducted by gravity-based dewatering system, a flocculation settling tank, a sequential batch reactor with supernatant collection, or a disk stack centrifuge. In an embodiment, supernatant or clarified fermentation broth is forwarded to the filter pressing step described herein.

In an embodiment, the coarse filtration system comprises a rotary drum vacuum filter (RVDF). In an embodiment, the coarse filtration system comprise a RVDF and a filter press, and the RVDF is used prior to the filter press. When the RVDF is operating in a semi-continuous mode, the cake is continuously scraped off the RVDF's membrane surface. In an embodiment, the RVDF is in semi-continuous mode, thereby the cake is continuously scraped off the membrane surface of the RVDF. In an embodiment, the filtrate is loaded into a filter press or into cold storage for fine filtration. In a specific embodiment, the coarse filtration system comprises operation unit 200 and/or 202 in FIG. 10.

Any Coarse filtration method herein refers to the operation unit 200/202 shown in FIG. 10. In an embodiment, the coarse filtration system comprises a screw press, a pressure-induced dead-end filtration system, or a pressure-based dewatering system. In an embodiment, the pressure-based dewatering system comprises a basket strainer, a screw press, a sieve, or a filter bag.

Any fine filtration method herein refers to the operation unit 204/206 shown in FIG. 10. In an embodiment, operation unit 204/206 may include an assembly of a feed tank and filter cartridges. In an embodiment, a hollow fiber or tubular membrane cartridges are used for cross-flow filtration. In an embodiment, the fermentation broth filtrate is circulated at constant flow rate from a feed tank through a hollow fiber membrane cartridge of pore size about 0.22 µm-300,000 NMWC. In an embodiment, the system is arranged into a plurality of cartridges in parallel. In an embodiment, the cartridge is about 30-60 cm in length and about 0.5-1.5 mm in lumen diameter. In an embodiment, the cartridge comprises polysulfone material membrane. In an embodiment, permeate from broth passing through the membrane is cold storage. In an embodiment, the permeate is fed to PHA-producing bacteria. Retentate is broth that is not filtered and circulates back into the fine filtration system's feed tank. In an embodiment, retentate is concentrated as the permeate is recovered. In an embodiment, the fine filtration is in batch mode, meaning that the fine filtration feed tank is completely drained before refilling. In an embodiment, when in batch mode, about at most 10% (v/v) of initial broth volume is discarded as concentrated retentate. In an embodiment, semi-continuous and continuous mode, where fine filtration feed tank is refilled at predetermined volumes or intervals, yields higher retentate recovery.

In an embodiment, microfiltration or ultrafiltration membrane comprises variations. In an embodiment, variations comprise a water purification membrane system. In an embodiment, the water purification membrane is in cross flow or dead-end flow configuration. In an embodiment, the water purification membrane comprises a reverse osmosis system, a dead-end tubular membrane cartridge, and an electrodialysis system.

In an embodiment, coarse filtration is followed by fine filtration. In an embodiment, coarse filtration comprises a screw press or other pressure-induced dead-end filtration systems. In an embodiment, coarse filtration comprises pressure-based dewatering systems. In an embodiment, pressure-based dewatering systems comprises basket strainers, screw press, sieves, or filter bags.

In an aspect, the second step of filtration involves a fine microfiltration (also known as microfiltration or ultrafiltration), wherein the fermentation broth is transferred using an appropriate transfer mechanism 414 as seen in FIG. 4 & FIG. 10, and wherein the fermentation broth is filtered through a fine filter 204/206 (Refers to FIG. 10) with a pore size ranging from 0.2 µm to 500,000 NMWC, optionally with cut-off as low as 300,000 NMWC, to remove the acidogenic fermentative bacteria and undigested organic waste, to obtain a clarified broth comprising concentrated VFAs. In another aspect, fine microfiltration described herein refers to, for example, the operation unit 204/206 shown in the FIG. 10. The microfiltration or ultrafiltration is performed similarly at the larger process scale, wherein a fine filter, optionally a multiple cartridge membrane filter, with a pore size ranging from 0.2 µm to 500,000 NMWC 204/206 (refer to FIG. 10) is optionally used. The advantage of using a two-step filtering system (operation units 200/202 and 204/206 respectively in FIG. 10) is to reduce the risk of clogging the finer microfiltration or ultrafiltration filter and reduce the need for frequent filter cartridge replacement. Solids removed through the filtration process may be further processed, for example, into compost.

In an embodiment, VFA composition is analyzed, optionally by gas or liquid chromatography techniques or other appropriate methods. In an embodiment, VFA composition is analyzed by gas chromatography, optionally gas chromatography-mass spectrometry. In an embodiment, VFA composition is analyzed by liquid chromatography, optionally high performance liquid chromatography. Analysis is done, to confirm that the concentration of VFAs produced is as expected or to confirm VFA production quantity. Analysis allows for the clarified broth to be diluted achieving a desired VFA concentration, typically 30-90 Cmmol/L, optionally 30-60 VFA mmol/L or 90-180 Cmmol/L.

In an embodiment, the clarified broth contains VFAs at a concentration of at least 30 Cmmol/L. In an embodiment, the clarified broth contains VFAs at a concentration of at least about 30 mmol/L. In an embodiment, the clarified broth contains VFAs at a concentration of between about 30 VFA mmol/L and about 90 VFA mmol/L, about 90-180 Cmmol/L, or about or at least 400, 450, 500, 550, 600, 650, 700, 750, or 800 VFA mmol/L. In an embodiment, the clarified broth contains VFAs at a concentration of at least 1, 2, 3, 4, or 5 mol/L.

The methods described herein for PHA production use high-PHA producing bacteria. In an embodiment, high-PHA producing bacteria comprises aerobic PHA producing bacteria. In embodiment, aerobic PHA producing bacteria comprises bacteria from the genus Brachymonas, *Pseudomonas, Acinetobacter, Sphingomonas, Thauera*, or *Cyclobacteriaceae*, or a combination thereof. In an embodiment, the high-PHA producing bacteria converts VFA to PHA. In an embodiment, the PHA is polyhydroxybutyrate (PHB), optionally poly-3-hydroxybutyrate (P3HB), polyhydroxyvalerate (PHV), polyhydroxyhexonate (PHH), and/or poly (3-hydroxybutyric acid-co-3-hydroxyvaleric acid (PHBV). In an embodiment, the PHA is PHB. In an embodiment, the PHB is P3HB. In an embodiment, the PHA is PHV. In an embodiment, the PHA is PHH. In an embodiment, the PHA is PHBV.

It is readily apparent to the person skilled in the art how to assess the purity of the resulting albumin solution. For instance, gas and liquid chromatography analysis described herein may be carried out to assess the purity of PHA. In an embodiment, the purity of PHA is about or at least 85, 90, 91, 92, 93, 94, 95, 96, 97, 98, 99, 99.5, or 99.9%. In an embodiment, the purity of PHA is about or at least 95%.

Extracted PHA can be further purified. In an embodiment, PHA is treated in a reflux at about 100° C. for about 150 min in the presence of chloroform, methanol, and sulfuric acid. In an embodiment, PHA is converted into methyl esters.

Figure 3:
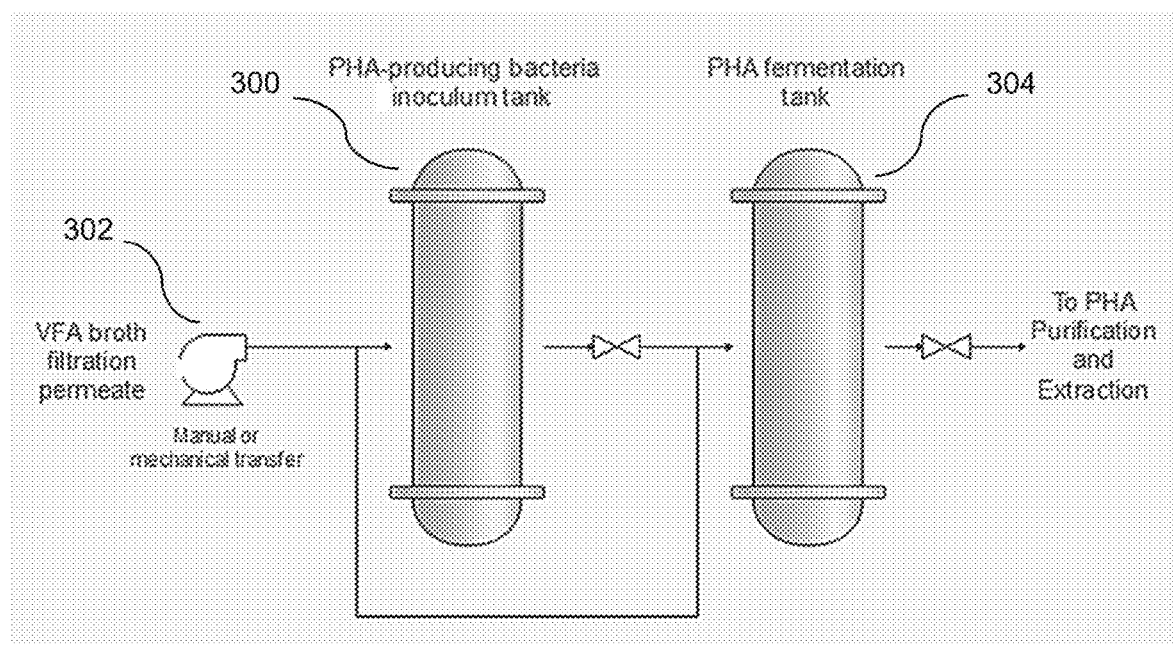
FIG. 3 is a process flow diagram of PHA-producing bacteria growth and PHA fermentation.

After the filtering step, for example FIG. 10, high-PHA producing bacteria that produce high amounts of PHA are selected, wherein the selecting comprises feast famine incubation in order to obtain high-PHA producing bacteria. In an embodiment, after the filtering step, high-PHA producing bacteria that produce high amounts of PHA are selected, wherein the selecting comprises feast famine incubation in order to obtain high-PHA producing bacteria. The selecting process may also be done as an ongoing process that does not have to necessarily follow the filtration step (operation unit 200/202 and 204/206 in FIG. 10). Feast famine incubation can be continuously maintained in order to obtain a constant supply of new cells. The bacterial community may change over time to become more efficient. The selection of high-PHA producing bacteria is done in a high-PHA producing bacteria inoculum tank 300 as exemplified in FIG. 3 (also refers to FIG. 11) under specific conditions as described below. An example of a high-PHA producing bacteria inoculum tank 300 (also referred to FIG. 11) may be a semi-continuous mode stirred tank or otherwise an agitated reactor, ensuring a fully aerobic environment. Bubble column reactors, stirred tank reactors, or airlift reactors may also be used.

Figure 11:
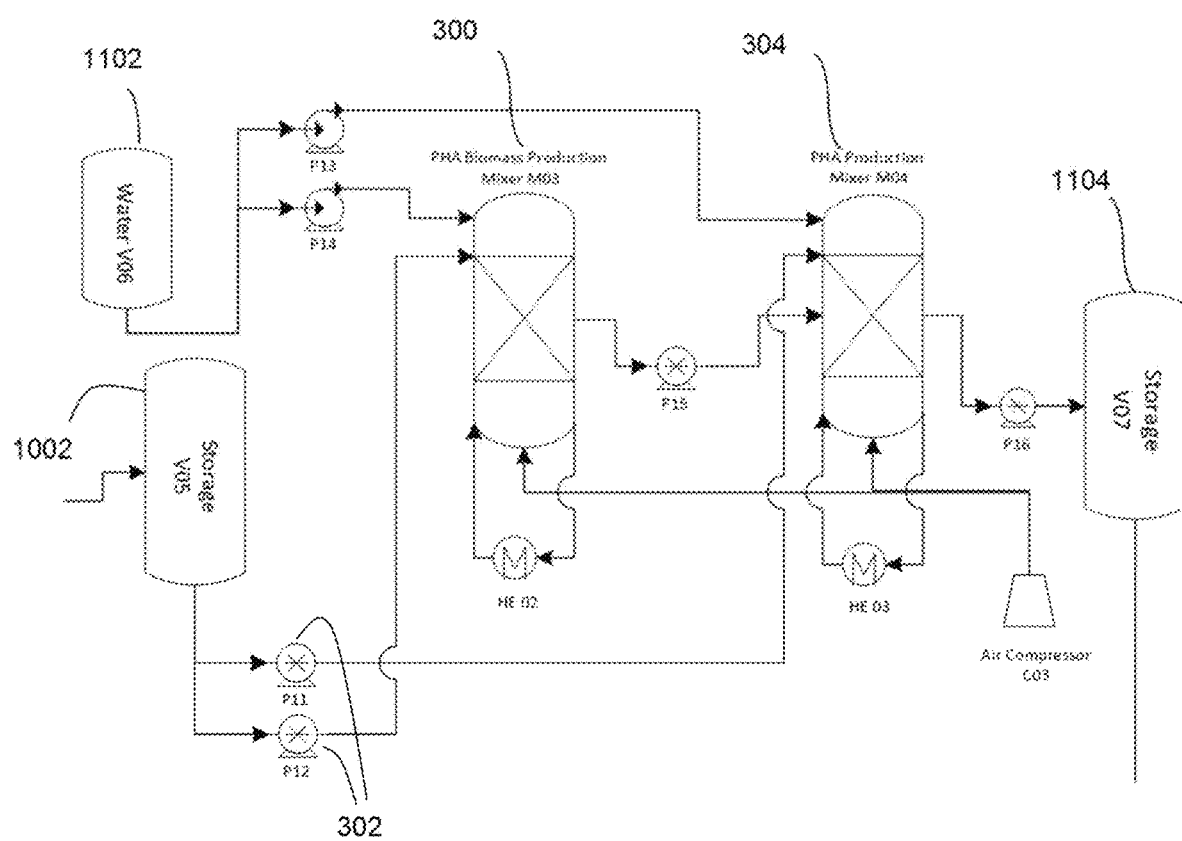
FIG. 11 is a detailed block flow diagram of PHA-producing biomass accumulation and PHA production stages, both conducted in aerobic fermenters.

FIG. 11 shows an exemplary embodiment of flow of PHA-producing biomass accumulation (refer to operation unit 300 in FIG. 11) and PHA production stages (refer to operation unit 304 in FIG. 11), both conducted in aerobic fermenters.

In an embodiment, the feast famine incubation comprises incubating the high-PHA producing bacteria in the clarified broth, a first group of suitable nutrients, and an environmental sample taken for example from wastewater treatment plant sludge. A manual or an appropriate mechanical transfer mechanism 302 (Refer to FIG. 11) is used to transfer the clarified broth, the first suitable nutrients and the environmental sample to the high-PHA producing bacteria inoculum tank 300 (refer to FIG. 11).

The feast famine incubation referred to herein is an incubation process, wherein a PHA-producing bacterial culture, derived from an environmental sample optionally wastewater treatment plant sludge, is fed clarified fermentation broth and a burst of nutrients and consumes the carbon source (VFAs) until depleted. This depletion of carbon sources marks the beginning of the famine stage. High-PHA producing bacteria can take up carbon during the feast phase and store it as PHA in intracellular granules. This allows the PHA-producing bacteria to continue growing using the stored PHA for energy even after the VFAs are depleted. This provides a selective advantage over other bacteria that cannot store carbon for later use. Typically, there is a positive relationship between the time of running the mixed culture under feast famine incubation and obtaining very selective and highly adapted PHA producing bacterial strains. For the purposes of selecting high-PHA producing bacteria in this method, the feast famine incubation may optionally range from a period of about 6 to 18 months. Once high-PHA producing bacteria are obtained, they may be continuously cultured indefinitely.

In an embodiment, the feast famine process comprises replacing a portion, optionally half or less, of a mixture of the clarified broth, the first group of suitable nutrients, and the PHA-producing bacteria about every 6-36 h, optionally about every: 6 h, 10 h, 12 h, 18 h, 24 h, 30 h, or 36 h with a fresh batch of the clarified broth and the first group of suitable nutrients.

In an embodiment, the clarified broth comprises VFAs at 30-90 Cmmol/L, optionally 30-60 VFA mmol/L or 90-180 Cmmol/L, and the first suitable group of nutrients comprising ammonium chloride ($NH_4Cl$), monobasic potassium phosphate ($KH_2PO_4$) and dibasic potassium phosphate ($K_2HPO_4$), and/or thiourea at 0.010 g/L. In an embodiment, the ratio of carbon to nitrogen ranges from 100:5 to 100:12 and the ratio of carbon to phosphorus ranges from 100:0.5 to 100:2. External addition of nutrients that are lacking in the VFA fermentation broth is done in order to ensure the optimal growth of PHA producing bacteria. If they are already present in sufficient quantity in the broth, nutrients may not be added.

In an embodiment, the clarified broth contains an approximate VFA composition of about: 20-60% (w/v) acetic acid, 5-30% (w/v) propionic acid, and 20-60% (w/v) butyric acid, as exemplified in FIGS. 14A-14C. In an embodiment, the clarified broth contains an approximate VFA composition of about: 20-60% (w/v) acetic acid, 5-30% (w/v) propionic acid, and 20-60% (w/v) butyric acid. The content of the different VFAs in the clarified broth can vary with the source and composition of the organic waste used, as well as the types of bacteria present and the conditions used during the acidogenic fermentation.

In an embodiment, the selecting of the high-PHA producing bacteria is done under pH conditions of 6-9, optionally 6-7 or 7-8, or 8-9 and temperature conditions of 20-40° C., optionally 20-25° C., or 25-30° C., or 30-35° C., or 35-40° C.

In an embodiment, once the high-PHA producing bacteria are selected, and in order to produce the PHA, the high-PHA producing bacteria are combined with the clarified broth and a second group of nutrients comprising VFAs at: 30-90 Cmmol/L, optionally 30-60 VFA mmol/L or 90-180 Cmmol/L, $KH_2PO_4$ and $K_2HPO_4$, and/or thiourea at 0.010 g/L, with a carbon to phosphorus ratio of 100:0.5 to 100:2. Similarly to the step of high-PHA producing bacteria selection, nutrients may not be added if they are already present in sufficient quantity in the broth.

In an embodiment, the mixture of the clarified broth, the second group of suitable nutrients and the high-PHA producing bacteria are incubated in a PHA fermentation tank 304 (Refer to FIG. 11) to produce intracellular PHA granules under pH conditions of 6-9, optionally 6-7 or 7-8, or 8-9, temperature conditions of 20-40° C., optionally 20-25° C., or 25-30° C., or 30-35° C., or 35-40° C. and incubation times of 1-24 h, optionally 1-3 h, or 3-6 h, or 6-9 h, or 9-12 h, or 12-18 h, or 18-24 h. Similarly to the high-PHA producing bacteria selection process, incubation of the high-PHA producing bacteria may use bubble column reactors, stirred tank reactors, or airlift reactors, preferably airlift reactors. PHA production is done under aerobic conditions.

In an embodiment, the method of culturing high-PHA producing bacteria for producing PHA comprises, culturing the high-PHA producing bacteria in a culture media containing suitable nutrients, VFA at 30-60 mmol/L, a carbon source, and a nitrogen source maintaining pH at 6-9, optionally 6-7, 7-8, or 8-9, and maintaining a temperature of between about 20 and 40° C., optionally between about 20 and 25° C., 25 and 30° C., 30 and 35° C., or 35 and 40° C., for between about 1-24 h, optionally 1-3 h, 3-6 h, 6-9 h, 9-12 h, 12-18 h, or 18-24 h.

In an embodiment, the high-PHA producing bacteria is inoculated at about 4 g/L to about 20 g/L, optionally about 4 g/L to about 18 g/L.

The PHAs are typically accumulated in the form of granules. The PHA polymers are stored inside of the cells as discrete granules that are water-insoluble. In an embodiment, the accumulation of PHA granules is monitored, optionally by fluorescence spectroscopy analysis of the PHA producing culture. In an embodiment, the cells are fixed by heating a smear of the PHA producing culture, which is the liquid mixture that contains the PHA producing bacteria, on a glass slide. The heat-fixed cells can then be stained with 1% (v/v) aqueous Nile Blue A solution, or another appropriate staining solution and washed with sequences of water, acetic acid and water again. Afterward, the fixed culture can be analyzed using fluorescence microscopy as PHA granules will fluoresce under these conditions (see FIG. 5). Optionally, a high throughput Nile Red assay may be used to monitor and quantify the intracellular PHA granules in a liquid culture using fluorescence spectroscopy as exemplified in FIGS. 16A-16F and FIG. 0.17.

Figure 12:
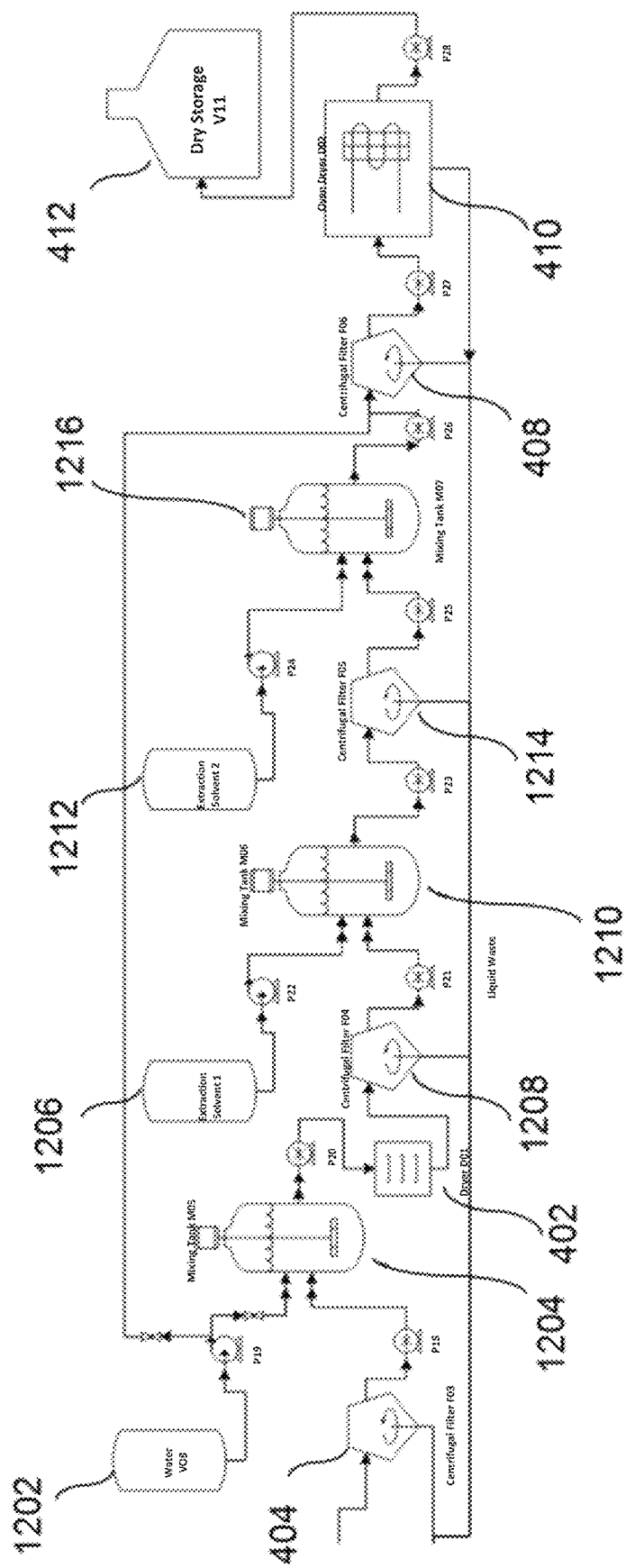
FIG. 12 is a detailed block flow diagram of PHA granule extraction and purification process. The process includes cell harvesting, solvent washes, product drying and storage. A lyophilizer (Dryer D01) is optionally used for cell lysis.

In an aspect, PHA polymers are extracted with sequential washes for up to 3 times and lyophilized with a lyophilizer 402 (Refer to FIG. 12). In an embodiment, the PHA polymers are extracted with sequential washes for up to 3 times and lyophilized with a lyophilizer for about 48 h at temperatures of −20 to −80° C., optionally −30 to −35° C., −35 to −40° C., −40 to −45° C., or −45 to −50° C. PHA extraction step described herein refers to FIG. 12 and/or FIG. 13. Centrifugation or microfiltration with an appropriate centrifuge and microfilter 404 for purification, may also be used during PHA granule extraction. The skilled person can readily recognize the appropriate centrifuge and microfilter. An appropriate transfer mechanism 416 may be used to transfer the liquid waste removed during centrifugation or microfiltration for wastewater treatment. The skilled person can readily recognize the teachings in the figures described here for centrifugation and mixing steps, for example, operation units 404, 1208/1308, 1214/1314, 408, and 1204/1304, 1210/1310, 1216/1316.

Embodiments of the invention will be described in a non-limiting manner by reference to the examples below.

EXAMPLES

Example 1: Sequential Extraction

Sequential surfactant-hypochlorite digestion or chloroform-hypochlorite dispersion can be employed for extracting PHA from PHA-producing bacteria. For sequential surfactant-hypochlorite digestion, PHA is extracted by treating 30 g cell mass in 1 L of SDS (10 g/L) at 55° C. for 10-60 min, where the dissolved solution starts to appear cloudy towards the end.

The cell mass dissolved in SDS is centrifuged at 10,000× g, and the pellet washed twice each with double distilled water ($ddH_2O$) and acetone and treated with 12% (v/v) sodium hypochlorite (NaOCl) for 2-15 min. The solution is centrifuged at 10,000×g, and the pellet of purified PHA washed twice each with $ddH_2O$ and acetone and dried for 24 h at 55° C.

For chloroform-hypochlorite dispersion, 1 g of dried cell mass is incubated with a dispersion containing 50 mL of chloroform and 50 mL of 12% (v/v) sodium hypochlorite solution (optionally 25 mL of each) in water, in an orbital shaker at 100 rpm at 38° C. for 0.5-2 h. The mixture obtained is then centrifuged at 4000×g for 10-30 min, which results in three separate phases. The PHA is recovered from the bottom phase, i.e. that of chloroform by precipitation using 10 volumes of ice-cold methanol. The precipitate obtained is centrifuged at 4000×g for 10-30 min, and washed twice each with $ddH_2O$ and acetone and dried for 24 h under 55° C. The purity of the extracted polymer can be tested under fourier-transform infrared spectroscopy (FTIR), gas chromatography (GC-MS), high performance liquid chromatography (HPLC), and proton nuclear magnetic resonance ($^1HNMR$) spectroscopy. For GC-MS and HPLC analysis, the polymer will be broken down to its monomer components in the presence of methanol, concentrated sulfuric acid and chloroform.

Figure 13:
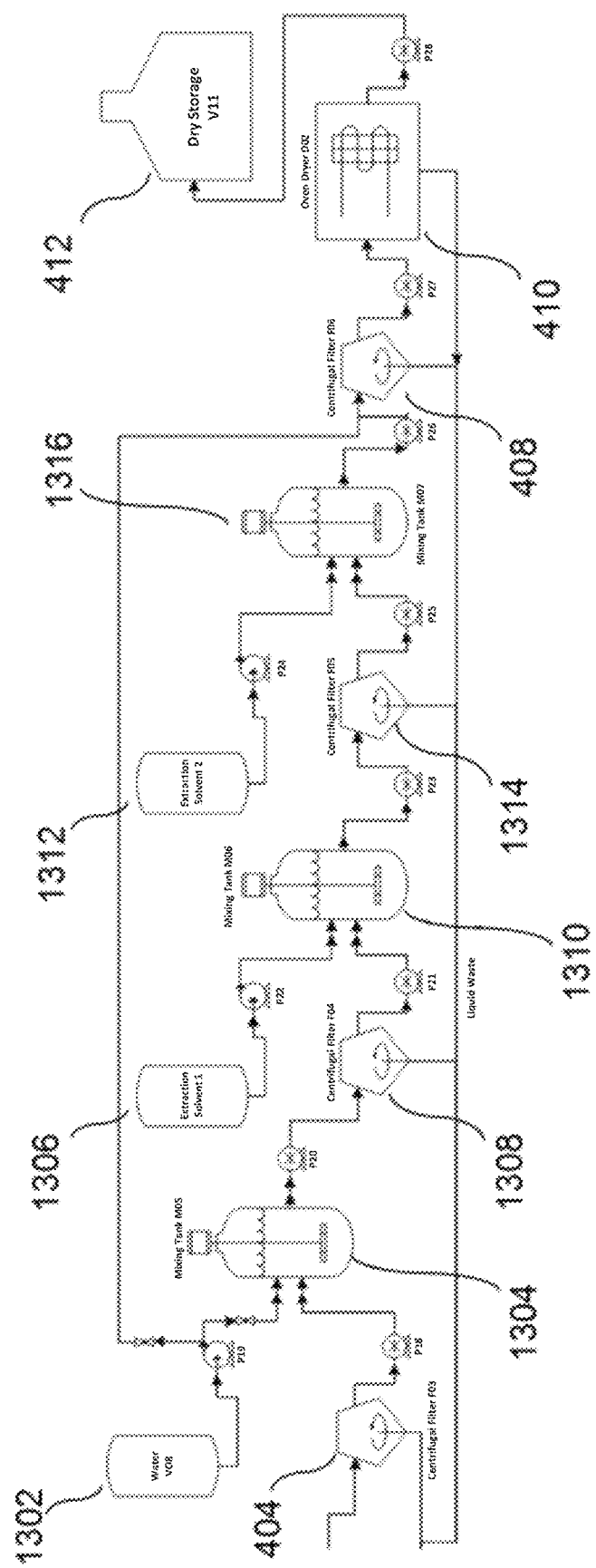
FIG. 13 is a detailed block flow of PHA granule extraction and purification process. The process includes cell harvesting, solvent washes, product drying and storage. Optionally, no lyophilizer is used for cell lysis.
Figure 15A:
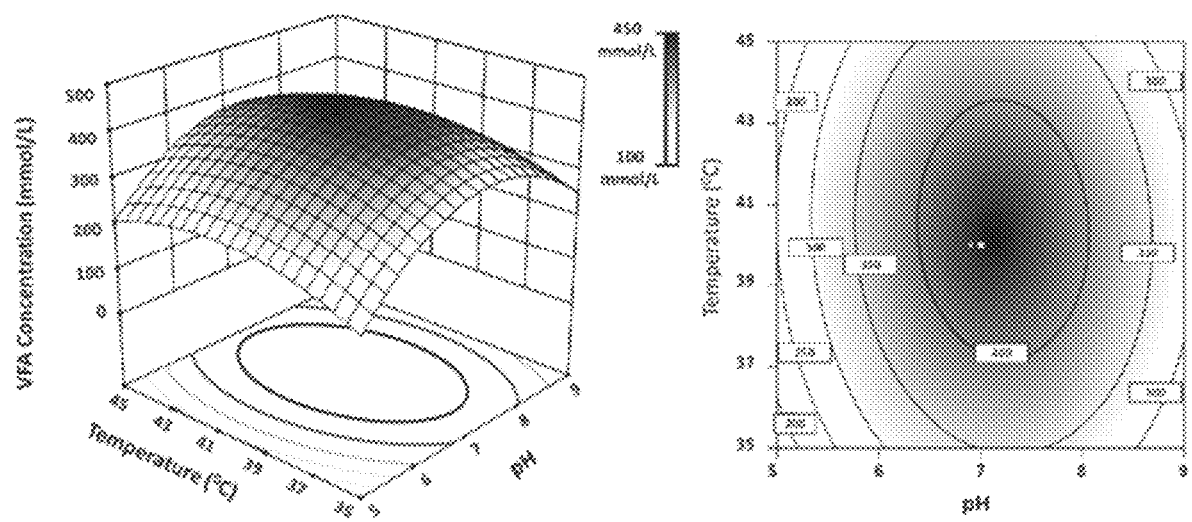
FIGS. 15A-15C show a plurality of graphs depicting surface and contour plot.
Figure 15B:
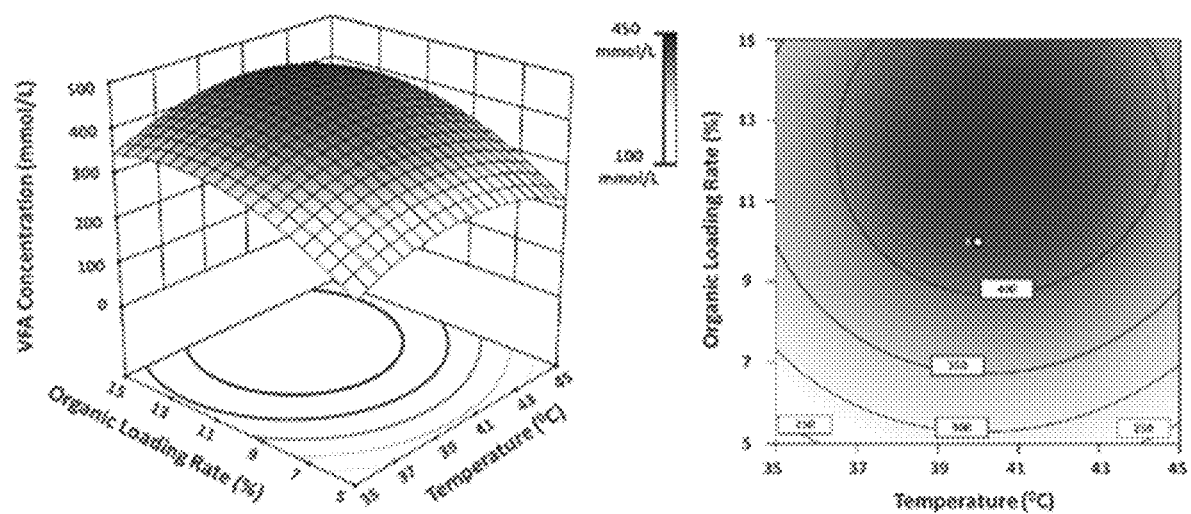
Figure 15C:
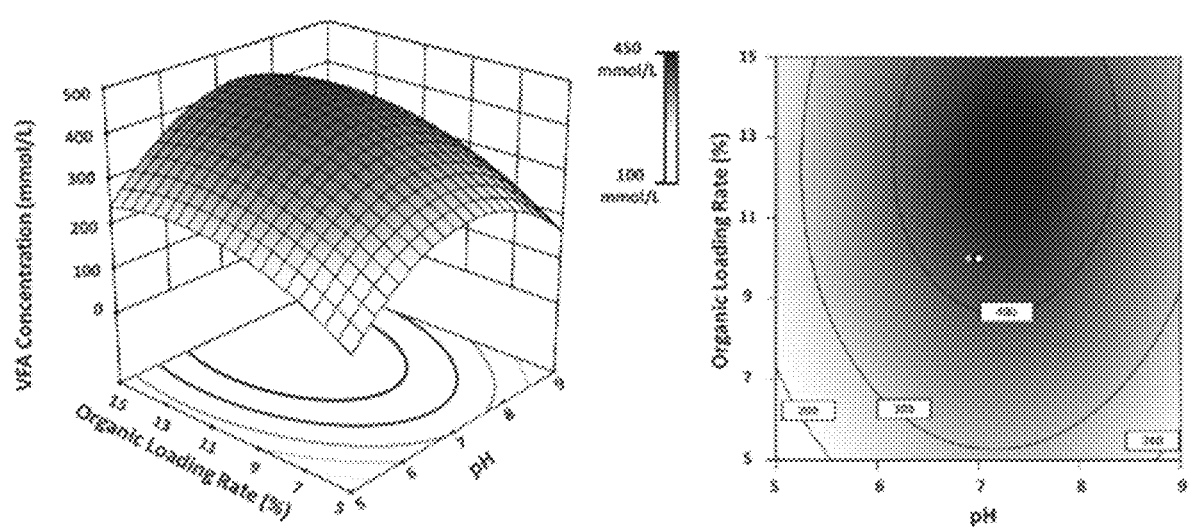
Figures 16A, 16B, 16C:
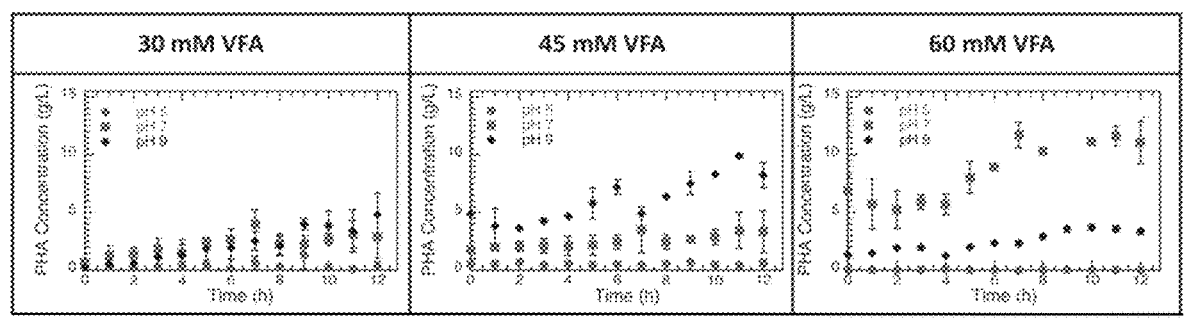
FIGS. 16A-16F show a plurality of graphs depicting time-resolved evolution of PHA production and cell density changes as a function of varying VFA feed concentrations and pH.
Figures 16D, 16E, 16F:
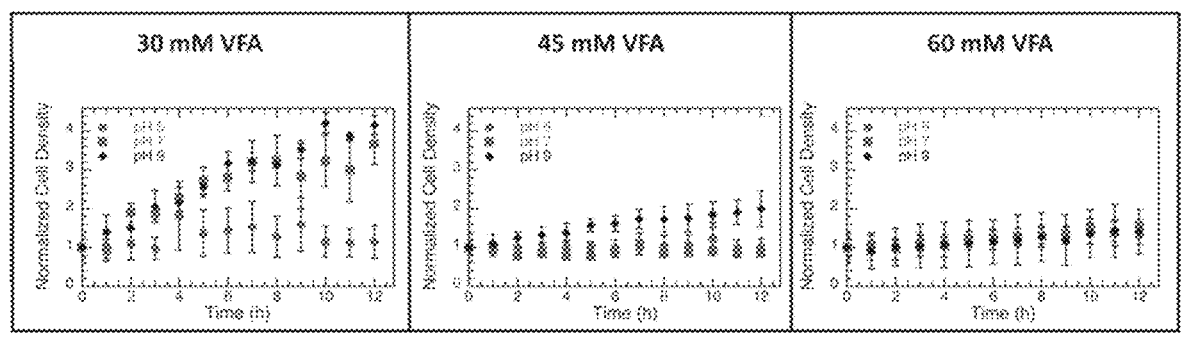
Figure 17:
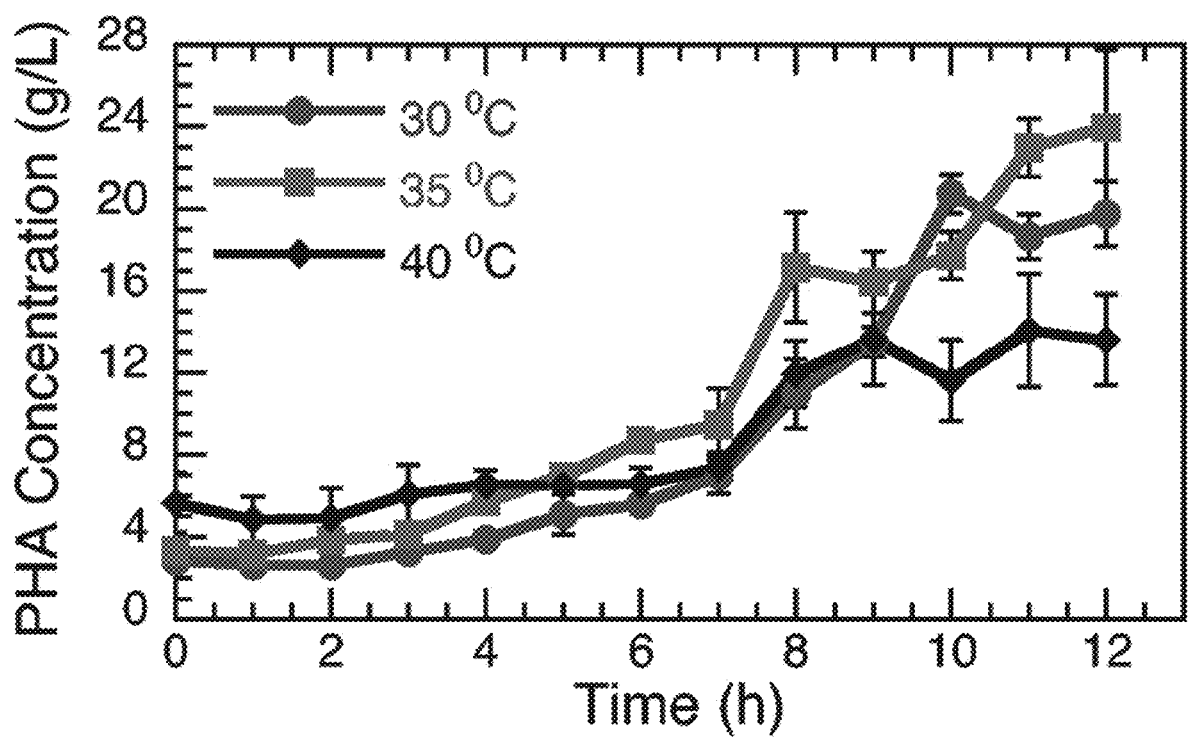
FIG. 17 is a graph depicting time-resolved PHA production curves at varying temperatures at pH 7 and 60 VFA mmol/L.

Finally granules undergo solvent/water washing and purification in appropriate equipment 406 (see Water and Extraction Solvent tanks in FIG. 12 and FIG. 13, respectively) and sequential centrifugation in a centrifuge 404, 1208/1308, 1214/1314 and 408 (Refer to FIG. 12 and FIG. 13) followed by mechanical drying via spray dryer 410 (refer to FIG. 12 and FIG. 13) or other low temperature appropriate methods before product storage in a granule storage tank 412 (refer to FIG. 12 and FIG. 13).

Example 2: Inoculum Sources

Initial testing of different inoculum sources for the acidogenic fermentation showed some variation in the quantity of VFAs produced from different inoculums. The highest concentration of VFAs was achieved with an inoculum of animal manure, followed by wastewater treatment plant sludge. Sediment samples produced the lowest concentration of VFAs. Mixing the three inoculum sources resulted in VFA production slightly lower, optionally less than 10% lower, than the manure-only fermentation. VFA composition was similar among all inoculum sources. Butyric and acetic acid were the dominant VFAs produced, in amounts of about 60-90% (w/v) acetic and butyric acid as exemplified in FIGS. 14A-14C. A small amount, optionally about 10-40% of propionic acid was also produced from all inoculum sources. The inoculum sources likely varied in VFA yield due to differences in the quantity or diversity of anaerobic microorganisms in the source material.

Further testing assesses the effects of pH on VFA yield under controlled ORP conditions (FIGS. 14A-14C). Acetic acid and butyric acid were the dominant VFAs produced at all pH levels produced in amounts of about 60-90% (w/v) acetic and butyric acid, along with a smaller proportion of propionic acid at about 10% (w/v) of propionic acid (FIGS. 14A-14C).

One of skill in the art can readily adjust temperature, pH, and ORP of an apparatus described herein to follow the parameters disclosed herein for VFA production.

During testing the coarse filter pore size was 200 μm and the fine filter pore size was 0.2 μm.

Example 3: Feast-Famine Process

Figure 5:
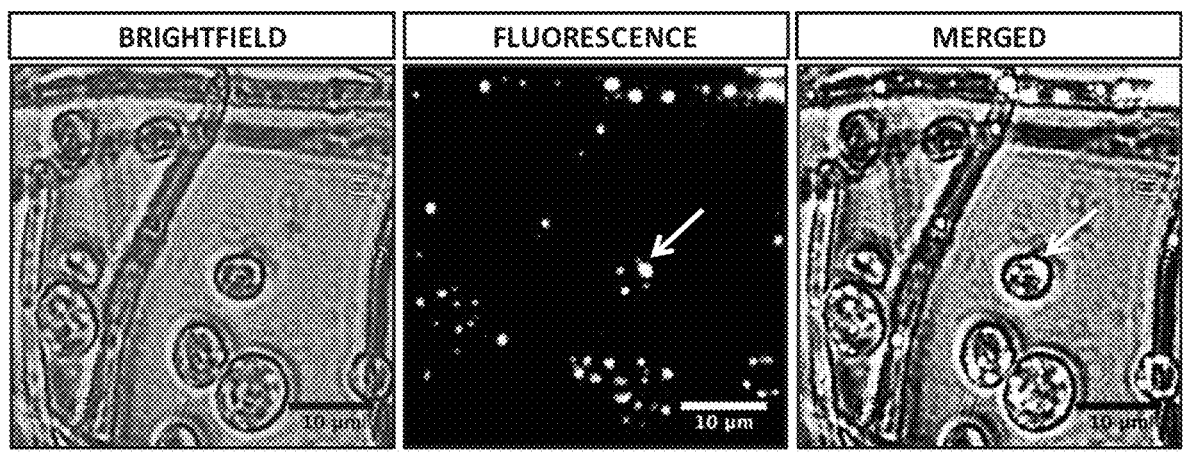
FIG. 5 shows representative brightfield, fluorescence and merged images of a fixed culture of PHA producing bacteria. The white dots on the fluorescence image represent the stained intracellular PHA granules (shown by the corresponding arrows).
Figure 6A:
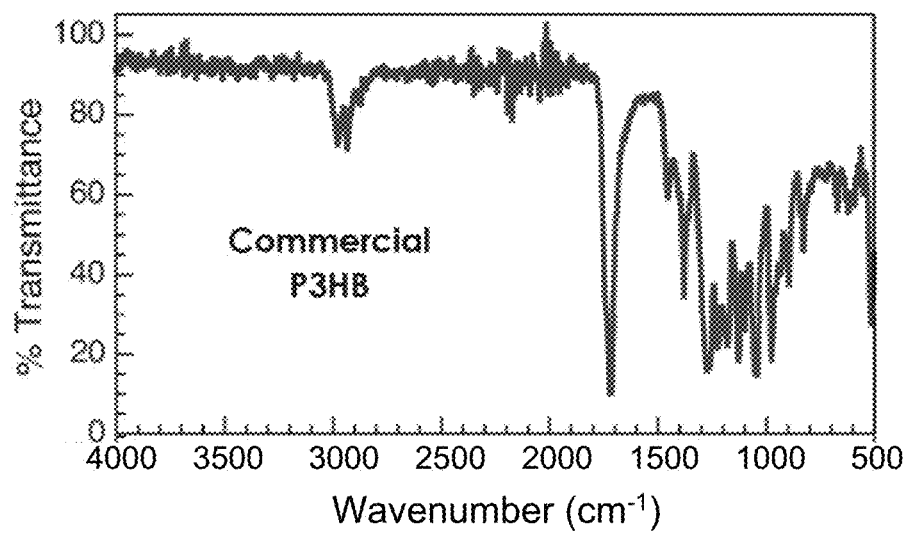
FIGS. 6A and 6B show two fourier-transform infrared spectroscopy (FTIR) spectra of PHA.
Figure 6B:
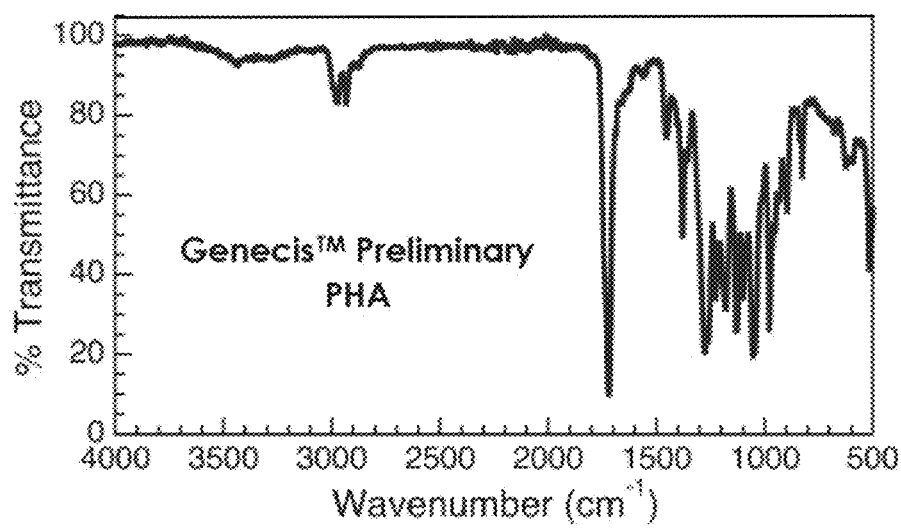

An automated feast-famine process was utilized to select the adapted PHA producing microbial species from the mixed continuous culture. Microbes (e.g. bacteria) that can effectively convert organic acids to PHA storage material under aerobic and pH neutral conditions were isolated. An increase in the amount of intracellular PHA content was observed post 90 days of running the continuous mixed culture (FIG. 5). Once an optimal PHA producing continuous culture was obtained, supplemented organic acids were added and the time evolution (1-24 h) of the intracellular PHA content accumulation was evaluated in situ using fluorescent microscopy, and fluorescence spectroscopy (FIGS. 16A-16F and FIG. 17).

Example 4: Conversion Process of Organic Waste to VFAs

Figure 18:
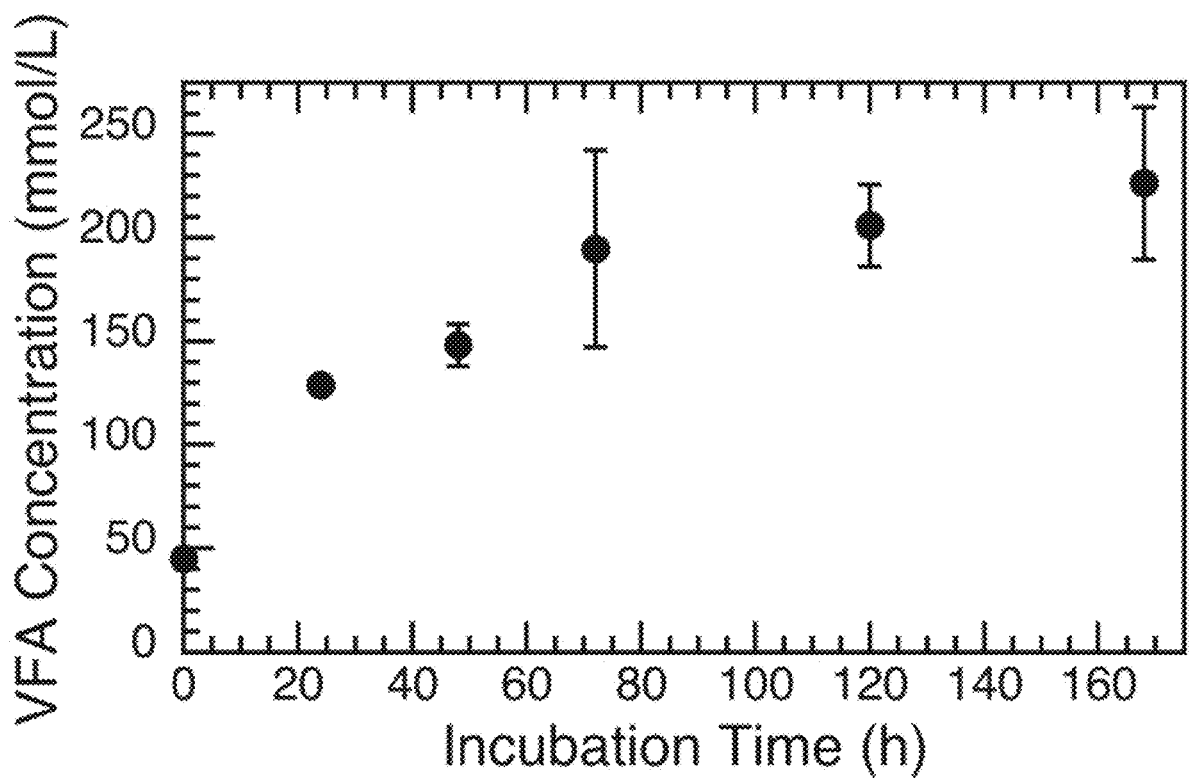
FIG. 18 is a graph depicting time-resolved VFA yields at varying incubation times. The graph depicts average and standard deviation of two trials.
Figure 19:
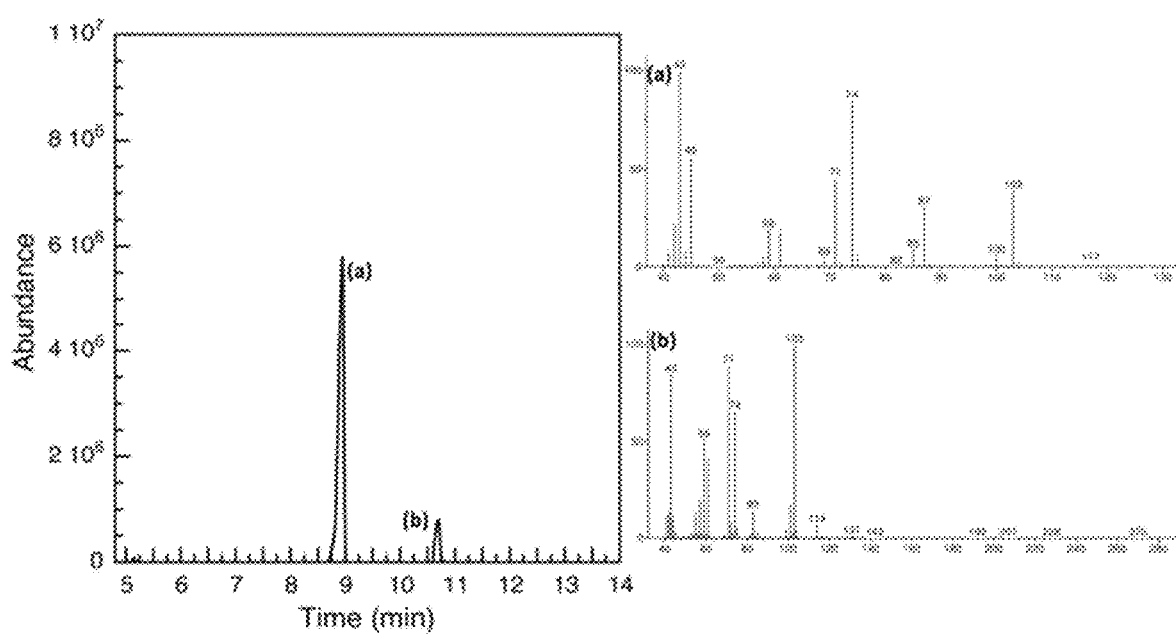
FIG. 19 depicts a Gas Chromatography Mass Spectrometry (GC-MS) analysis of the extracted PHA polymer post methanolysis treatment, where methanolysis treatment refers to the treatment of the PHA polymer in a reflux at 100° C. for 150 min in the presence of chloroform, methanol, and sulfuric acid.

The performance of the conversion process of organic waste to VFAs was assessed based on i) the ability of the acidogenic fermentative bacteria to rapidly convert organic waste into VFAs, ii) the final yield of VFAs from the feedstock of organic waste, and iii) the relative composition of the individual VFAs produced. Post-fermentation, the fermentation broth was filtered to remove any particulates above 0.2 μm, and the filtered broth is then quantified using HPLC, prior to feeding it to the PHA fermentation tank. Additionally, the inoculated feedstock was also tested for incubation of up to 7 days, to obtain a fermentation broth that contains VFAs (see FIG. 18). The results show that an incubation time of as short as 3 days, or 3-5 days, is optimal for to obtain higher yields of VFA in the fermentation broth (see FIG. 18). All the experiments herein below in this Example were conducted with a 3 day incubation time, and the experimentations showed the optimal ranges of temperature (40-42° C.), pH (7-8), and organic loading rates (10-15% (w/w)) to produce VFAs at high efficiencies (see FIGS. 14A-14C, 15A, 15B and 15C), for example, for at least 400-450 VFA mmol/L, and up to or above VFA 800 mmol/L.

In a further experiment, feedstock was pre-treated with thermal (50-65° C.) and acidic (pH 2-3) treatments for 6-12 h prior to the fermentation step for determining resulting VFA yield. This pre-treatment had an effect on the corresponding VFA yields.

Example 5: Flocculation

Figure 20:
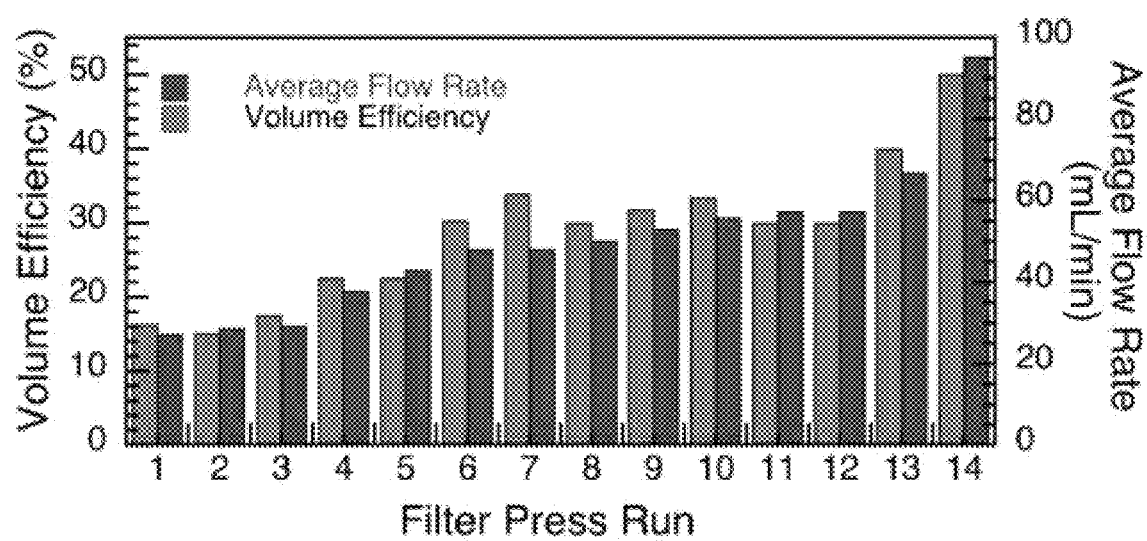
FIG. 20 is a graphical representation of the filter press coarse filtration of fermentation broth. Varying the loading rate was tested to reflect the incremental improvement of filtration efficiency. Flow rate is determined as fermentation broth volume loaded over filtration time. Volume efficiency is defined as filtrate volume obtained over fermentation broth volume loaded.

Fermentation broth was produced as described in Example 4. Filtration was carried out as described in Methods and Apparatus section. Filter press coarse filtration of fermentation broth with or without flocculation was evaluated. Loading rate was varied and tested to reflect the improvement of filtration efficiency. Operating pressure was also varied and tested. Flow rate was determined as broth volume loaded over filtration time. Volume efficiency was defined as filtrate volume obtained over fermentation broth volume loaded. Filter press run 1-3: 30 L of fermentation broth was loaded; filter press run 4-5: 40 L of fermentation broth was loaded; and filter press run 6-14: 48 L of fermentation broth was loaded in to the filter press. Results are shown in FIG. 20. Filter press run 14 refers to the fermentation broth treated with flocculant prior to filtration, showing further improvement in volume efficiency and average flow rate with flocculation.

Example 6: Continuous PHA-Producing Bacterial Culture

Continuous PHA-producing bacterial culture with VFA concentration of 30-60 VFA mmol/L or 90-180 Cmmol/L, supplemented with the second group of nutrients at 35° C. and pH 7 was used to maintain selective pressure on the PHA-producing bacteria. This is followed by a batch culture where the PHA-producing bacteria accumulate PHA (FIGS. 5, 6A, 6B, 7, and 19). Both the biomass accumulation, semi-continuous fermenter (Refer to 300 in FIG. 11) and the PHA batch production fermenter (Refer to 304 in FIG. 11) were monitored for normalized cell density and temperature. Normalization process for cell density was done by taking the cell density at a given time point and dividing it by the cell density at time zero. Several airlift reactor design configurations were tested to identify optimal mass transfer coefficient, heat transfer coefficient, and solids suspension. This allowed for validation of the use of air-mixed reactors for PHA cultures, thus greatly reducing the operation and maintenance cost of this operation unit, while maintaining the option of mechanical mixing as backup. Scale-up is thus based on oxygen mass transfer rate coefficient (kLa), superficial gas velocity and volumetric air flow as opposed to tip speed used for anaerobic digester (refer to 106 in FIG. 9). The PHA cell density in the batch reactor, which is identical in design to the semi-continuous airlift reactor described in Methods and Apparatus, was 20-50 g/L and the intracellular PHA content varies between 40-70%. Based on high-throughput Nile Red test conducted, the optimal parameters for PHA production were found to be temperature at 30-35° C., pH at 7-9, VFA concentration of 30-240 VFA mmol/L or 90-720 Cmmol/L consisting of the second group of suitable nutrients, and incubation times of 6-12 h (FIGS. 16A-16F and 17).

Example 7: PHA Production

In the industry, the production of PHA polymers is not as cost efficient as traditional petrochemical plastics. The presence of high levels of impurities and the low product yields can significantly hamper the downstream industrial processing of PHA. Thus improving the extraction yield and lowering the PHA extraction costs and impurities is desirable. In the present study, PHA recovery from the mixed culture was evaluated using various extraction techniques (i.e. sequential chemical digestion, chloroform-hypochlorite extraction). Many effective organic solvent based PHA recovery techniques are studied in the literature.

Chemical digestion approaches utilize sodium hypochlorite (NaOCl) or surfactants (for example sodium dodecyl sulphate (SDS), Triton X-100™, lithium alkyl sulphate (LAS), palmitoyl carnitine, or betaine) to solubilize and digest PHA producing cellular mass and aid with the PHA extraction. Sodium hypochlorite is a strong oxidizing agent. However, its corresponding non-selective oxidization can be manipulated to only digest PHA producing cellular mass and facilitate PHA recovery by controlling the NaOCl concentration and treatment time. Isolating PHA granules by surfactant digestion have shown to have lower degree of purity but a slightly higher molecular weight than hypochlorite digestion. In contrast, hypochlorite digestion produces PHA of higher purity but can severely degrade the PHA molecular weight. The quality of PHA obtained using either the surfactant or sodium hypochlorite recovery techniques is not optimal for industrial standards, thus moving towards a sequential surfactant-hypochlorite digestion.

A range of parameters (i.e. temperature, treatment time, pH and concentrations) for surfactant (for example SDS or non-ionic surfactant Triton X-100™) and hypochlorite were tested and the yield and purity of the recovered PHA was then evaluated. Post-SDS solubilization, the remaining recovered PHA was treated with NaOCl at a range of incubation times and concentrations. At 55° C., pH of 11 and an incubation time of 15 min, increasing the SDS concentration from 5 to 15 g/L increased the extracted yield by 51 to 79% respectively. SDS at 10 g/L was used for the remainder of the study. Although the recovery of PHA with SDS treatment was highly effective in solubilizing and removing lipid, protein and other biomacromolecular content from disrupted cells, the non-solubilized peptidoglycan and other debris can bind to the hydrophobic surface of PHA granules and can disrupt the PHA purity, which can affect the PHA tensile strain properties and yielding discoloured products during processing of the polymer.

Figure 7:
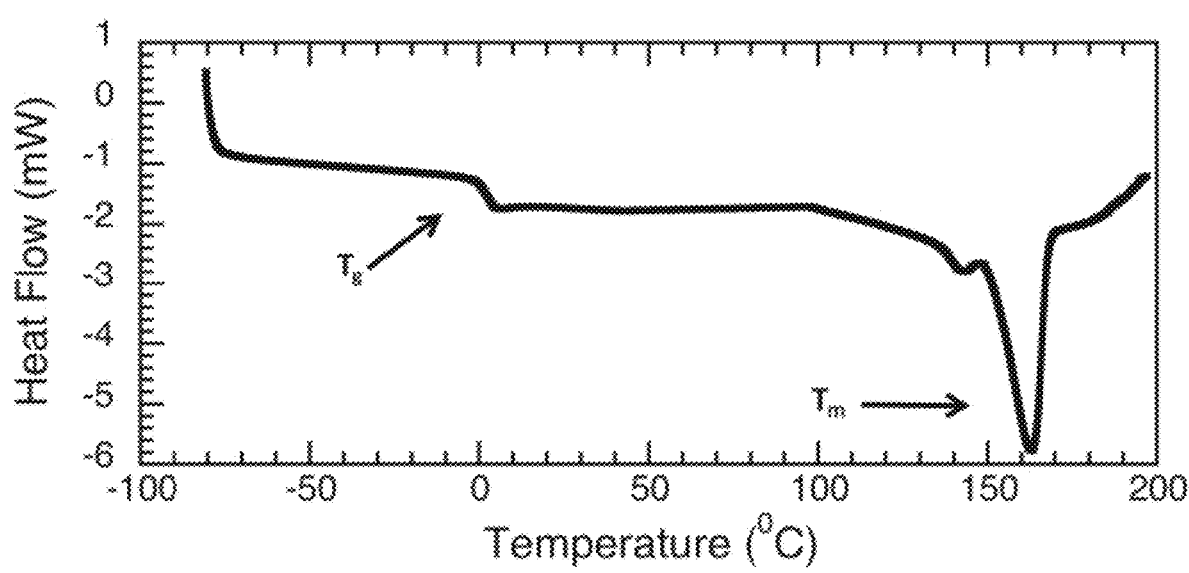
FIG. 7 is a graph depicting thermochemical characterization of the PHAs. The graph shows melting point ($T_m$) and glass transition temperature ($T_g$).

Further purification was achieved with the use of sequential NaOCl treatment. The effect of the different NaOCl concentrations and treatment times on the purity and yield of PHA were evaluated. After washing the isolated PHA three times with water, ethanol and acetone, the extracted and purified polymer appeared as a white powder. Short treatment times and relatively low concentrations of NaOCl (5-12% v/v of OCl$^-$) decreased the effect of non-PHA biomass degradation (FIGS. 6A and 6B), preserving its thermochemical properties (FIG. 7). FIG. 7 shows thermochemical characterization of the PHAs, depicting melting point ($T_m$) and glass transition temperature ($T_g$). At 12% v/v NaOCl and with an incubation time of 15 min, the purity of the extracted PHA was found to be 95%. The extracted PHA was then treated in a reflux at 100° C. for 150 min in the presence of chloroform, methanol, and sulfuric acid. The PHA is then converted into methyl esters which facilitates the separation of different hydroxyalkanoate present in the copolymer structure for further analysis. Based on gas chromatography mass spectroscopy (GC-MS), PHA copolymers composed of PHB and PHV were obtained (see FIG. 19).

Example 8: Accelerated Process of Converting Organic Waste to PHA

Figure 21:
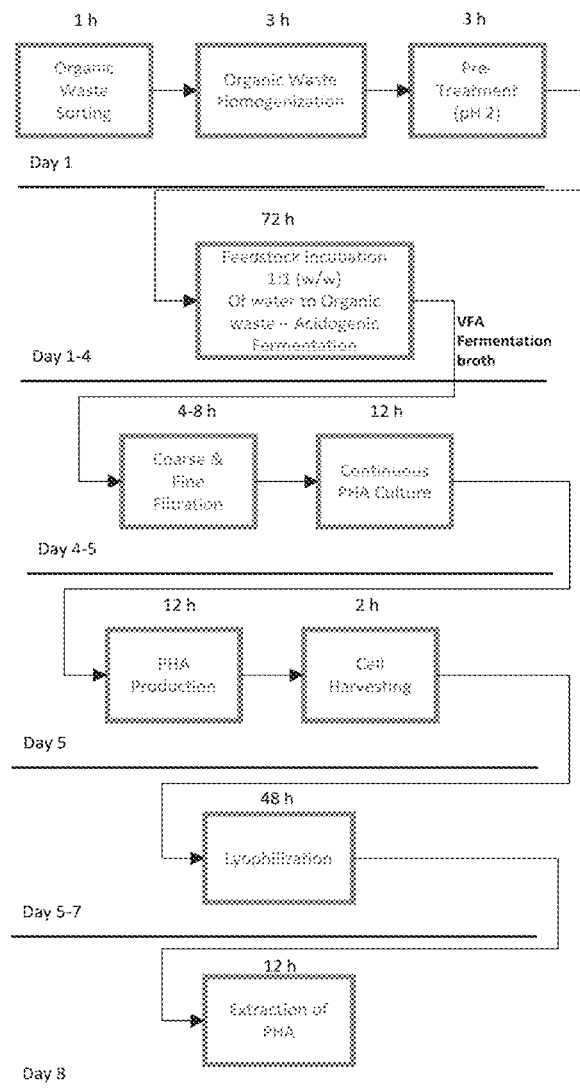
FIG. 21 is block flow diagram of accelerated process of converting organic waste to PHA as described in Example 8.

The accelerated process of converting organic waste to PHA was carried out within 7-10 days and was conducted with 40 kg of organic waste (see FIG. 21). The process was started by sorting the organic waste manually (1 h) homogenizing the sorted organic waste using a garburator (2-3 h), and pre-treating the feedstock with an acidic treatment of pH 2-3 for a time of 3 h. The pre-treated feedstock was then adjusted to a 1:1 (w/w) water to organic waste ratio. The resulting feedstock was incubated with an acidogenic continuous inoculum at 40° C., while maintaining the pH at 7, the OLR at 10%, and an uncontrollable ORP of 0--900 mV, for a period of 72 h in order to obtain fermentation broth consisting of concentrated VFAs, yielding 420 VFA mmol/L. The resulting fermentation broth was filtered through coarse (filter press with a 0.5 μm cut off) and fine filtration (gravity cartridges with a 0.2 μm cut off) to obtain a clarified broth comprising of concentrated VFAs (8 h). A diluted clarified broth containing 60 VFA mmol/L was incubated with the continuous PHA-producing bacteria in a semi-continuous culture to maintain selective pressure on the PHA producing bacteria (12 h) at 35° C. at pH 7. 240 VFA mmol/L of clarified broth was incubated with high-PHA producing bacteria in a batch culture at 35° C. and pH 7 to produce intracellular PHA granules in the high-PHA producing bacteria (12 h). Afterwards, the high-PHA producing bacterial cells were harvested (2 h), and lyophilized for 48 h as described in operation unit 402 in FIG. 12. The intracellular PHA granules were extracted from the lyophilized PHA producing cell mass using the sequential SDS and NaOCl technique described in example 7 (12 h), yielding 400 g of PHBV (see FIG. 19).

While the present disclosure has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

REFERENCES

Bharti, S. N., & Swetha, G. (2016) Need for Bioplastics and Role of Biopolymer PHB: A Short Review. J Pet Environ Biotechnol 7, 272

By, P. U. C., Roland-Holst, D., Triolo, R., Heft-Neal, S., & Bayrami, B. (2013). Bioplastics in California.

Chanprateep, S. (2010). Current trends in biodegradable polyhydroxyalkanoates. Journal of bioscience and bioengineering, 110, 621-632.

Chen, G. Q. (2009). A microbial polyhydroxyalkanoates (PHA) based bio- and materials industry. Chemical Society Reviews, 38, 2434-2446.

Dong, Z., & Sun, X. (2000). A new method of recovering polyhydroxyalkanoate from *Azotobacter chroococcum*. Chinese Science Bulletin, 45, 252-256.

Hahn, S. K., & Chang, Y. K. (1995). A themogravimetric analysis for poly (3-hydroxybutyrate) quantification. Biotechnology techniques, 9, 873-878.

Hahn, S. K., Chang, Y. K., Kim, B. S., Lee, K. M., & Chang, H. N. (1993). The recovery of poly (3-hydroxybutyrate) by using dispersions of sodium hypochlorite solution and chloroform. Biotechnology techniques, 7, 209-212.

Hazer, D. B., Kiligay, E., & Hazer, B. (2012). Poly (3-hydroxyalkanoate) s: diversification and biomedical applications: a state of the art review. Materials Science and Engineering: C, 32, 637-647.

Ramsay, J. A., Berger, E., Ramsay, B. A., & Chavarie, C. (1990). Recovery of poly-3-hydroxyalkanoic acid granules by a surfactant-hypochlorite treatment. Biotechnology Techniques, 4, 221-226.

Reis, M. A. M., Serafim, L. S., Lemos, P. C., Ramos, A. M., Aguiar, F. R., & Van Loosdrecht, M. C. M. (2003). Production of polyhydroxyalkanoates by mixed microbial cultures. Bioprocess and biosystems engineering, 25, 377-385.

Salehizadeh, H., & Van Loosdrecht, M. C. M. (2004). Production of polyhydroxyalkanoates by mixed culture: recent trends and biotechnological importance. Biotechnology advances, 22, 261-279.

Valappil, S. P., Misra, S. K., Boccaccini, A. R., & Roy, I. (2006). Biomedical applications of polyhydroxyalkanoates, an overview of animal testing and in vivo responses. Expert Review of Medical Devices, 3, 853-868

Yu, P. H., Chua, H., & Huang, P. A. L. (1999, December). Conversion of food industrial wastes into bioplastics with municipal activated sludge. In Macromolecular Symposia (Vol. 148, No. 1, pp. 415-424). WILEY-VCH Verlag GmbH & Co. KGaA.

Yu, P. H., Chua, H., Huang, A. L., Lo, W., & Chen, G. Q. (1998). Conversion of food industrial wastes into bioplastics. Applied biochemistry and biotechnology, 70, 603-614.

Zuriani, R., Vigneswari, S., Azizan, M. N. M., Majid, M. I. A., & Amirul, A. A. (2013). A high throughput Nile red fluorescence method for rapid quantification of intracellular bacterial polyhydroxyalkanoates. Biotechnology and bioprocess engineering, 18, 472-478.

The invention claimed is:

1. A method for producing polyhydroxyalkanoates (PHA) from organic waste comprising:
   homogenizing organic waste to obtain a feedstock that has a 1:1 to 3:1 (w/w) water to organic waste ratio, wherein the homogenizing comprises mechanical particle reduction;
   inoculating the feedstock with an inoculum of acidogenic fermentative bacteria in order to obtain an inoculated feedstock;
   incubating the inoculated feedstock for 3 to 10 days under pH conditions of 6-8, temperature conditions of about 40-42° C., and organic loading rate of about 10-15% to obtain a fermentation broth, wherein the fermentation broth comprises at least about 400 mmol/L volatile fatty acids (VFAs) and undigested organic waste;
   adding a flocculant to the fermentation broth;
   coarse filtering the fermentation broth with a coarse filter with a pore size of at least 0.5 μm for reducing the risk of clogging of fine filter;
   fine filtering the coarse-filtered fermentation broth with a fine filter with a pore size of at most 0.22 μm, or a fine filter that is a cartridge rated for at most at 500,000 NMWC, to remove the acidogenic fermentative bacteria and undigested organic waste, to obtain a clarified broth comprising concentrated VFAs, wherein the clarified broth contains a VFA composition of about: 20-60% acetic acid, 5-30% propionic acid, and 20-60% butyric acid;
   incubating, a PHA producing bacteria from an environmental sample, in the clarified broth comprising a first group of nutrients, wherein the PHA producing bacteria is subjected to a feast famine process that comprises removing a portion of a mixture of the clarified broth, the first group of nutrients, and the PHA-producing bacteria, about every 6-36 h, and adding an additional batch of the clarified broth comprising the first group of nutrients, wherein the clarified broth and the first group of nutrients comprise VFAs at 30-90 Cmmol/L or 90-180 Cmmol/L, or 30-60 VFA mmol/L, NH4Cl, KH2PO4 and K2HPO4, with a carbon to nitrogen ratio of 100:5 to 100:12 and with a carbon to phosphorus ratio of 100:0.5 to 100:2, and wherein the clarified broth contains a VFA composition of about: 20-60% acetic acid, 5-30% propionic acid, and 20-60% butyric acid;
   incubating the clarified broth and PHA producing bacteria to produce intracellular PHA granules in the PHA producing bacteria;
   extracting PHA polymers from the intracellular PHA granules.

2. The method of claim 1, wherein the mechanical particle reduction comprises using a food garburator, a grinder, and/or a mill for producing a ratio of water to organic waste of about 1:1 to 3:1 (w/w), wherein the inoculum is selected from wastewater treatment plant sludge, animal manure, and/or sediments and oxygen reduction potential (ORP) conditions of 0 to −300 mV.

3. The method of claim 1, wherein the fine filtering step comprises gravity filtration, pressure/flowrate-driven filtration through a cross-flow microfiltration membrane, or dead-end filtration, and further comprising, following the homogenizing step, filtering the feedstock with a filter with a pore size between about 100 μm to about 200 μm, to adjust the feedstock to the 1:1 to 3:1 (w/w) water to organic waste ratio.

4. The method of claim 1, wherein the coarse filter is a rotary vacuum filter, or filter press.

5. The method of claim 1, wherein the environmental sample is wastewater treatment plant sludge.

6. The method of claim 1, wherein the clarified broth and the first group of nutrients further comprise thiourea at 0.010 g/L.

7. The method of claim 1, wherein the selecting of the PHA producing bacteria is done under pH conditions of 6-9 and temperature conditions of 20-40° C.

8. The method of claim 1, further comprises combining the PHA producing bacteria with the clarified broth and a second group of nutrients comprise VFAs at: 30-90 Cmmol/L or 30-240 VFA mmol/L, KH2PO4 and K2HPO4, with a carbon to phosphorus ratio of 100:0.5 to 100:2.

9. The method of claim 8, wherein the incubating of the clarified broth, the second group of suitable nutrients and the PHA producing bacteria to produce intracellular PHA granules is done under pH conditions of 6-9 temperature conditions of 20-40° C., and incubation times of 1-24 h.

10. The method of claim 1, wherein the accumulation of PHA granules is monitored, optionally by fluorescence spectroscopy analysis of a PHA producing culture.

11. The method of claim 1, wherein the extracting of the PHA polymers is done with sequential washes for up to 3 times and lyophilization for 48 h at a temperatures of −20 to −80° C.

12. The method of claim 1, wherein the organic waste is pretreated by thermal, acid, and/or enzymatic treatments.

13. The method of claim 1, further comprising analysis of the VFA composition by gas or liquid chromatography, and the clarified broth is adjusted to achieve a desired VFA concentration.

14. The method of claim 1, wherein the PHA polymers is polyhydroxybutyrate (PHB), poly-3-hydroxybutyrate (P3HB), polyhydroxyvalerate (PHV), polyhydroxyhexonate (PHH), and/or poly(3-hydroxybutyric acid-co-3-hydroxy-valeric acid (PHBV).

15. The method of claim 8, wherein the second group of nutrients further comprises thiourea at 0.010 g/L.

16. The method of claim 2, wherein the mill is a hammer mill.

\* \* \* \* \*